United States Patent
Chang et al.

(10) Patent No.: US 11,638,517 B2
(45) Date of Patent: May 2, 2023

(54) SYSTEMS AND METHODS FOR MEDICAL IMAGING USING A ROLLING SHUTTER IMAGER

(71) Applicant: Stryker Corporation, Kalamazoo, MI (US)

(72) Inventors: William Huei Liang Chang, Milpitas, CA (US); Bryan Larson, San Jose, CA (US); John Shen, San Jose, CA (US); Benjamin Feingold, Tucson, AZ (US); Ajay Ramesh, Pleasanton, CA (US)

(73) Assignee: Stryker Corporation, Kalamazoo, MI (US)

( * ) Notice: Subject to any disclaimer, the term of this patent is extended or adjusted under 35 U.S.C. 154(b) by 219 days.

(21) Appl. No.: 16/745,154

(22) Filed: Jan. 16, 2020

(65) Prior Publication Data
US 2020/0234439 A1    Jul. 23, 2020

Related U.S. Application Data

(60) Provisional application No. 62/793,790, filed on Jan. 17, 2019.

(51) Int. Cl.
*H04N 5/374* (2011.01)
*A61B 1/045* (2006.01)
(Continued)

(52) U.S. Cl.
CPC ........ *A61B 1/045* (2013.01); *A61B 1/000095* (2022.02); *A61B 1/043* (2013.01);
(Continued)

(58) Field of Classification Search
CPC ......... G06T 7/0012; G06T 2207/10068; G06T 2207/30004; A61B 1/00009; A61B 1/043;
(Continued)

(56) References Cited

U.S. PATENT DOCUMENTS

| 3,289,957 A | 12/1966 | Hans-gunter et al. |
| 6,293,911 B1 | 9/2001 | Imaizumi |

(Continued)

FOREIGN PATENT DOCUMENTS

| EP | 3289957 A1 | 3/2018 |
| WO | 2010059197 A2 | 5/2010 |
| WO | 2014018936 A2 | 1/2014 |

OTHER PUBLICATIONS

International Preliminary Report on Patentability dated Jun. 16, 2021, directed to International Application No. PCT/US2020/013912; 13 pages.

(Continued)

*Primary Examiner* — Howard D Brown, Jr.
(74) *Attorney, Agent, or Firm* — Morrison & Foerster LLP

(57) ABSTRACT

A method of imaging tissue of a subject using an electronic rolling shutter imager includes sequentially resetting rows of pixels of the rolling shutter imager from a first row to a last row, sequentially reading charge accumulated at the rows of pixels from the first row to the last row, wherein the first row is read after resetting the last row, illuminating the tissue of the subject with illumination light for an illumination period that lasts longer than a vertical blanking period, wherein the vertical blanking period is the period from the resetting of the last row to the reading of the first row, and generating an image frame from the readings of charge accumulated at the rows of pixels, wherein at least one reading of charge accumulated at a row of pixels is removed or replaced to generate the image frame.

19 Claims, 12 Drawing Sheets

(51) Int. Cl.
*A61B 1/04* (2006.01)
*A61B 1/06* (2006.01)
*G06T 7/00* (2017.01)
*H04N 5/353* (2011.01)
*H04N 5/225* (2006.01)
*H04N 5/235* (2006.01)
*A61B 1/00* (2006.01)

(52) U.S. Cl.
CPC .......... *A61B 1/0684* (2013.01); *G06T 7/0012* (2013.01); *H04N 5/2256* (2013.01); *H04N 5/2354* (2013.01); *H04N 5/3532* (2013.01); *G06T 2207/10068* (2013.01); *G06T 2207/30004* (2013.01); *H04N 2005/2255* (2013.01)

(58) Field of Classification Search
CPC ..... A61B 1/045; A61B 1/0684; A61B 5/0084; A61B 5/414; A61B 5/0071; H04N 5/2256; H04N 5/2354; H04N 5/3532; H04N 2005/2255; H04N 5/3456; A61K 49/0034
See application file for complete search history.

(56) References Cited

U.S. PATENT DOCUMENTS

| | | | |
|---|---|---|---|
| 7,059,726 B2 | 6/2006 | Engle | |
| 7,179,222 B2 | 2/2007 | Imaizumi | |
| 7,397,509 B2* | 7/2008 | Krymski | H04N 5/335 348/308 |
| 7,479,990 B2 | 1/2009 | Imaizumi | |
| 8,540,626 B2 | 9/2013 | Seto et al. | |
| 8,550,990 B2 | 10/2013 | Seto et al. | |
| 9,060,404 B2 | 6/2015 | Upton | |
| 9,131,861 B2 | 9/2015 | Ince et al. | |
| 9,307,600 B2 | 4/2016 | Upton | |
| 9,531,156 B2 | 12/2016 | Hoffman et al. | |
| 11,347,189 B1* | 5/2022 | Herrera | G06F 3/016 |
| 2007/0221823 A1* | 9/2007 | Xu | H04N 5/363 348/E3.021 |
| 2010/0286529 A1 | 11/2010 | Carroll | |
| 2012/0013777 A1* | 1/2012 | Mao | H04N 9/04557 348/E9.01 |
| 2013/0208157 A1* | 8/2013 | Bechtel | H04N 5/235 348/297 |
| 2014/0078277 A1* | 3/2014 | Dai | H04N 5/2354 348/308 |
| 2014/0203170 A1 | 7/2014 | Ono et al. | |
| 2014/0225998 A1* | 8/2014 | Dai | H04N 5/2354 348/262 |
| 2014/0313386 A1* | 10/2014 | Jiang | H04N 5/35581 348/308 |
| 2015/0201871 A1* | 7/2015 | Shiraishi | G06T 7/0012 600/339 |
| 2015/0216460 A1* | 8/2015 | Shigeta | A61B 1/05 600/339 |
| 2015/0238086 A1* | 8/2015 | Saito | A61B 1/000094 600/339 |
| 2016/0374602 A1* | 12/2016 | Koshiba | H04N 5/23245 600/327 |
| 2017/0035280 A1* | 2/2017 | Yang | A61B 1/0646 |
| 2019/0324261 A1* | 10/2019 | Ogawa | A61B 1/00045 |

OTHER PUBLICATIONS

International Search Report and Written Opinion dated Jun. 25, 2020, directed to International Application No. PCT/US2020/013912; 19 pages.

Invitation to Pay Additional Fees and, where Applicable, Protest Fee and Partial Search dated Apr. 28, 2020, directed to International Application No. PCT/US2020/013912; 13 pages.

* cited by examiner

SYSTEMS AND METHODS FOR MEDICAL IMAGING USING A ROLLING SHUTTER IMAGER

CROSS-REFERENCE TO RELATED APPLICATIONS

This application claims the benefit of U.S. Provisional Application No. 62/793,790, filed Jan. 17, 2019, the entire contents of which are hereby incorporated by reference herein.

FIELD OF THE INVENTION

The present disclosure relates generally to medical imaging, and more particularly to generating medical imaging.

BACKGROUND OF THE INVENTION

Medical systems, instruments or tools are utilized pre-surgery, during surgery, or post-operatively for various purposes. Some of these medical tools may be used in what are generally termed endoscopic procedures. For example, endoscopy in the medical field allows internal features of the body of a patient to be viewed without the use of traditional, fully invasive surgery. Endoscopic imaging systems incorporate endoscopes to enable a surgeon to view a surgical site, and endoscopic tools enable non-invasive surgery at the site. Endoscopes may be usable along with a camera system for processing the images received by the endoscope. An endoscopic camera system typically includes a camera head connected to a camera control unit (CCU) that processes input image data received from the image sensor of the camera and outputs the image data for display. The CCU may control an illuminator that generates illumination light provided to the imaged scene.

Various imager sensors may be used in endoscopic imaging systems, including charge-coupled device (CCD) sensors and complementary metal oxide semiconductor (CMOS) sensors. Construction of CCDs is generally more complex than the construction of CMOS sensors, and CMOS sensors may be built in high volume wafer fabrication facilities used for related technologies such as microprocessors and chip sets, and as a result, CMOS sensors often less costly than CCDs for similar performance. In addition to lower cost, the common fabrication processes used to create CMOS imagers permits a CMOS pixel array to be integrated on a single circuit with other electronic devices such as clock drivers, digital logic, analog/digital converters and other suitable electronics. The compact structures possible for a CMOS imager may also reduce space requirements and lower power consumption.

CMOS based imagers may utilize electronic rolling shutters to expose pixels in the sensor array. With an electronic rolling shutter, rows of pixels are cleared, exposed, and read out in sequence. During integration, a row of pixels is exposed to light energy and each pixel builds an electric charge corresponding to the amount and wavelengths of light impinging the pixel. Because the rows are activated and read out in sequence, there is an elapsed time between when the first row integrates and when the last row integrates. Because of the elapsed time between when the first row begins to integrate and when the subsequent rows begin to integrate, a CMOS imager with an electronic rolling shutter may capture video images with blur or other rolling shutter effects.

SUMMARY OF THE INVENTION

According to some embodiments, imaging systems and methods use an electronic rolling shutter imager and coordinate illumination provided to a target object, such as a target tissue of a subject, to create a global shutter effect at the electronic rolling shutter imager, which can provide the cost and performance advantages of rolling shutter imagers without the rolling shutter effects. According to some embodiments, illumination is provided in the period between the resetting of a last row of the imaging sensor for a frame period and the readout of the first row of the imaging sensor for the frame period, resulting in a global shutter-type effect. The illumination period extends beyond this period to increase the exposure time of the sensor for increased sensitivity. Readouts from rows that may include rolling shutter effects may be removed or replaced when generating the image frames. Illumination light may be pulsed according to the exposure needs of the imager.

According to some embodiments, an extended global shutter period is created by skipping every other readout/reset time so that each row integrates for two frames of the nominal frame rate. This may reduce the frame rate of generated images but increases the sensitivity, which can allow for lower lighting amounts. Illumination light may be pulsed according to the exposure needs of the imager.

According to some embodiments, a method of imaging tissue of a subject using an electronic rolling shutter imager includes sequentially resetting rows of pixels of the rolling shutter imager from a first row to a last row, sequentially reading charge accumulated at the rows of pixels from the first row to the last row, wherein the first row is read after resetting the last row, illuminating the tissue of the subject with illumination light for an illumination period that lasts longer than a vertical blanking period, wherein the vertical blanking period is the period from the resetting of the last row to the reading of the first row, and generating an image frame from the readings of charge accumulated at the rows of pixels, wherein at least one reading of charge accumulated at a row of pixels is removed or replaced to generate the image frame.

According to some embodiments, a method of operating an electronic rolling shutter imager, such as for imaging tissue of a subject, includes sequentially resetting rows of pixels of the rolling shutter imager from a first row to a last row, sequentially reading charge accumulated at the rows of pixels from the first row to the last row, wherein the first row is read after resetting the last row, illuminating the tissue of the subject with illumination light for an illumination period that lasts longer than a vertical blanking period, wherein the vertical blanking period is the period from the resetting of the last row to the reading of the first row, and generating an image frame from the readings of charge accumulated at the rows of pixels, wherein at least one reading of charge accumulated at a row of pixels is removed or replaced to generate the image frame.

In any of these embodiments, the illumination period may begin prior to the resetting of the last row.

In any of these embodiments, the illumination period may end after the reading of the first row.

In any of these embodiments, the illumination period may begin at least when the vertical blanking period begins.

In any of these embodiments, the illumination period may end at least when the vertical blanking period ends.

In any of these embodiments, at least a reading of charge accumulated at the first row of pixels may be removed or replaced to generate the image frame.

In any of these embodiments, at least a reading of charge accumulated at the last row of pixels may be removed or replaced to generate the image frame.

In any of these embodiments, the at least one reading of charge accumulated at a row of pixels may be replaced by at least one predetermined value to generate the image frame.

In any of these embodiments, at least one reading of charge accumulated at a row of pixels may be removed by cropping to generate the image frame.

In any of these embodiments, the tissue of the subject may be illuminated with visible light and the method may further include illuminating the tissue of the subject with fluorescence excitation light at least during a subsequent vertical blanking period and generating a fluorescence image frame based on light emitted from the tissue of the subject in response to the fluorescence excitation light.

In any of these embodiments, the method may further include administering a fluorescence imaging agent to the subject prior to generating the fluorescence image frame. The fluorescence imaging agent may thus be pre-administered when performing the method.

In any of these embodiments, the method may include illuminating the tissue of the subject with fluorescence excitation light and visible illumination light simultaneously during the illumination period.

In any of these embodiments, illuminating the tissue of the subject with illumination light may include pulsing the illumination light.

In any of these embodiments, the method may include controlling a pulse width of the pulsed illumination light based on readings of charge accumulated at the rows of pixels during a previous frame.

In any of these embodiments, the illumination light may be generated by at least one LED.

In any of these embodiments, the rolling shutter imager may be part of an endoscopic imager. The method of imaging tissue of a subject or the method of operating an electronic rolling shutter may exclude the step of inserting such endoscopic imager in a lumen.

In any of these embodiments, the rolling shutter imager may include a mechanical shutter and the mechanical shutter may remain at least partially open from before the illumination period begins until after the illumination period ends.

In any of these embodiments, the method may further include reducing an amount of light received at the rolling shutter imager by operating the mechanical shutter.

In any of these embodiments, the method may further include adjusting a gain of the rolling shutter imager based on readings of charge accumulated at the rows of pixels during a previous frame.

According to some embodiments, a system for imaging tissue of a subject may include an illumination source; and an imaging apparatus that comprises an electronic rolling shutter imager, the imaging apparatus being configured for sequentially resetting rows of pixels of the rolling shutter imager from a first row to a last row, sequentially reading charge accumulated at the rows of pixels from the first row to the last row, wherein the first row is read after resetting the last row, controlling the illumination source to illuminate the tissue of the subject for an illumination period that lasts longer than a vertical blanking period, wherein the vertical blanking period is the period from the resetting of the last row to the reading of the first row, and generating an image frame from the readings of charge accumulated at the rows of pixels, wherein at least one reading of charge accumulated at a row of pixels is removed or replaced to generate the image frame.

In any of these embodiments, the imaging apparatus may include a camera control unit connected to an imaging head that includes the rolling shutter imager.

In any of these embodiments, the illumination source may be configured for pulse width modulated illumination and the camera control unit generates a pulse width modulation waveform for controlling the illumination source.

In any of these embodiments, the imaging apparatus may be configured to control the illumination source so that the illumination period begins prior to the resetting of the last row.

In any of these embodiments, the imaging apparatus may be configured to control the illumination source so that the illumination period ends after the reading of the first row.

In any of these embodiments, the imaging apparatus may be configured to control the illumination source so that the illumination period begins at least when the vertical blanking period begins.

In any of these embodiments, the imaging apparatus may be configured to control the illumination source so that the illumination period ends at least when the vertical blanking period ends.

In any of these embodiments, the imaging apparatus may be configured to generate the image frame so that at least a reading of charge accumulated at the first row of pixels is removed or replaced to generate the image frame.

In any of these embodiments, the imaging apparatus may be configured to generate the image frame so that at least a reading of charge accumulated at the last row of pixels is removed or replaced to generate the image frame.

In any of these embodiments, the imaging apparatus may be configured to generate the image frame so that the at least one reading of charge accumulated at a row of pixels is replaced by at least one predetermined value to generate the image frame.

In any of these embodiments, the imaging apparatus may be configured to generate the image frame so that at least one reading of charge accumulated at a row of pixels is removed by cropping to generate the image frame.

In any of these embodiments, the imaging apparatus may be configured to control the illumination source to illuminate the tissue of the subject with visible light during the vertical blanking period, to illuminate the tissue of the subject with fluorescence excitation light at least during a subsequent vertical blanking period, and to generate a fluorescence image frame based on light emitted from the tissue of the subject in response to the fluorescence excitation light.

In any of these embodiments, the imaging apparatus may be configured to control the illumination source to illuminate the tissue of the subject with fluorescence excitation light and visible illumination light simultaneously during the illumination period.

In any of these embodiments, the illumination source may be configured for pulsing the illumination light.

In any of these embodiments, the imaging apparatus may be configured to control the illumination source for controlling a pulse width of the pulsed illumination light based on readings of charge accumulated at the rows of pixels during a previous frame.

In any of these embodiments, the illumination source may include at least one LED.

In any of these embodiments, the imaging apparatus may include an endoscopic imager.

In any of these embodiments, the rolling shutter imager may include a mechanical shutter and the imaging apparatus may be configured to control the mechanical shutter so that the mechanical shutter remains at least partially open from before the illumination period begins until after the illumination period ends.

In any of these embodiments, the imaging apparatus may be configured to reduce an amount of light received at the rolling shutter imager by operating the mechanical shutter.

In any of these embodiments, the imaging apparatus may be configured to adjust a gain of the rolling shutter imager based on readings of charge accumulated at the rows of pixels during a previous frame.

According to some embodiments, a method of imaging tissue of a subject using an electronic rolling shutter imager includes sequentially resetting rows of pixels of the rolling shutter imager from a first row to a last row, wherein the sequential resetting from the first row to the last row lasts a first amount of time, illuminating the tissue of the subject with illumination light over an illumination period that begins once the last row of the rolling shutter imager has been reset and lasts for at least the first amount of time, accumulating charge at the rows of pixels over at least the illumination period based on light that is received from the tissue of the subject while the tissue of the subject is illuminated with the illumination light, sequentially reading charge accumulated at the rows of pixels from the first row to the last row once the illumination period has ended; and generating an image frame from the readings of charge accumulated at the rows of pixels.

According to some embodiments, a method of operating an electronic rolling shutter imager, such as for imaging tissue of a subject, includes sequentially resetting rows of pixels of the rolling shutter imager from a first row to a last row, wherein the sequential resetting from the first row to the last row lasts a first amount of time, illuminating the tissue of the subject with illumination light over an illumination period that begins once the last row of the rolling shutter imager has been reset and lasts for at least the first amount of time, accumulating charge at the rows of pixels over at least the illumination period based on light that is received from the tissue of the subject while the tissue of the subject is illuminated with the illumination light, sequentially reading charge accumulated at the rows of pixels from the first row to the last row once the illumination period has ended; and generating an image frame from the readings of charge accumulated at the rows of pixels.

In any of these embodiments, illuminating the tissue of the subject with illumination light may include pulsing the illumination light.

In any of these embodiments, the method may further include controlling a pulse width of the pulsed illumination light based on readings of charge accumulated at the rows of pixels during a previous frame.

In any of these embodiments, each row of pixels may accumulate charge over the illumination period.

In any of these embodiments, each row of pixels may accumulate charge for at least twice the first amount of time.

In any of these embodiments, the illumination light may be generated by at least one LED.

In any of these embodiments, the rolling shutter imager may be part of an endoscopic imager. The method of imaging tissue of a subject or the method of operating an electronic rolling shutter may exclude the step of inserting such endoscopic imager in a lumen.

In any of these embodiments, the rolling shutter imager may include a mechanical shutter and the mechanical shutter may remain at least partially open from before the illumination begins until after the illumination period ends.

In any of these embodiments, the method may further include reducing an amount of light received at the rolling shutter imager by operating the mechanical shutter.

In any of these embodiments, the method may further include adjusting a gain of the rolling shutter imager based on readings of charge accumulated at the rows of pixels during a previous frame.

According to some embodiments, a system for imaging tissue of a subject includes an illumination source; and an imaging apparatus that comprises an electronic rolling shutter imager, the imaging apparatus being configured for sequentially resetting rows of pixels of the rolling shutter imager from a first row to a last row, wherein the sequential resetting from the first row to the last row lasts a first amount of time, controlling the illumination source to illuminate the tissue of the subject with illumination light over an illumination period that begins once the last row of the rolling shutter imager has been reset and lasts for at least the first amount of time, accumulating charge at the rows of pixels over at least the illumination period based on light that is received from the tissue of the subject while the tissue of the subject is illuminated with the illumination light, sequentially reading charge accumulated at the rows of pixels from the first row to the last row once the illumination period has ended, and generating an image frame from the readings of charge accumulated at the rows of pixels.

In any of these embodiments, the imaging apparatus may include a camera control unit connected to an imaging head that includes the rolling shutter imager.

In any of these embodiments, the illumination source may be configured for pulse width modulated illumination and the camera control unit generates a pulse width modulation waveform for controlling the illumination source.

In any of these embodiments, the imaging apparatus may be configured to control the illumination source for illuminating the tissue of the subject with pulsed illumination light.

In any of these embodiments, the imaging apparatus may be configured to control the illumination source for controlling a pulse width of the pulsed illumination light based on readings of charge accumulated at the rows of pixels during a previous frame.

In any of these embodiments, the imaging apparatus may be configured so that each row of pixels accumulates charge over the illumination period.

In any of these embodiments, the imaging apparatus may be configured so that each row of pixels accumulates charge for at least twice the first amount of time.

In any of these embodiments, the illumination source may include at least one LED.

In any of these embodiments, the imaging apparatus may include an endoscopic imager.

In any of these embodiments, the rolling shutter imager may include a mechanical shutter and the imaging apparatus may be configured to control the mechanical shutter to remain at least partially open from before the illumination begins until after the illumination period ends.

In any of these embodiments, the imaging apparatus may be configured to reduce an amount of light received at the rolling shutter imager by operating the mechanical shutter.

In any of these embodiments, the imaging apparatus may be configured to adjust a gain of the rolling shutter imager based on readings of charge accumulated at the rows of pixels during a previous frame.

According to some embodiments, a non-transitory tangible computer-readable medium may have computer-executable program code embedded thereon to perform any of the above methods.

According to some embodiments, a computer program product may include computer implementable instructions which when implemented by a programmable computer cause the computer to perform any of the above methods.

According to some embodiments, a kit for processing a time series of images of tissue of a subject includes any of the systems described above or the non-transitory tangible computer-readable medium described above and an imaging agent.

In any of these embodiments, the imaging agent may be a fluorescence imaging agent.

According to some embodiments, a fluorescence imaging agent is for use in any of the systems above, in any of the methods above, or in any of the kits above for imaging tissue.

In any of these embodiments, imaging tissue may include imaging the tissue during blood flow imaging, tissue perfusion imaging, lymphatic imaging, or a combination thereof.

In any of these embodiments, blood flow imaging, tissue perfusion imaging, and/or lymphatic imaging may include blood flow imaging, tissue perfusion imaging, and/or lymphatic imaging during an invasive medical procedure, a minimally invasive medical procedure, or during a non-invasive medical procedure.

In any of these embodiments, the invasive medical procedure may include a cardiac-related medical procedure or a reconstructive medical procedure.

In any of these embodiments, the cardiac-related medical procedure may include a cardiac coronary artery bypass graft (CABG) procedure.

In any of these embodiments, the CABG procedure may be on pump or off pump.

In any of these embodiments, the non-invasive medical procedure may include a wound care procedure.

In any of these embodiments, the lymphatic imaging may include identification of a lymph node, lymph node drainage, lymphatic mapping, or a combination thereof.

In any of these embodiments, the lymphatic imaging may relate to the female reproductive system.

According to some embodiments, any of the systems above, any of the methods above, any of the kits above, or any of the fluorescence agents above, are used for lymphatic imaging.

According to some embodiments, any of the systems above, any of the methods above, any of the kits above, or any of the fluorescence agents above, are used for blood flow imaging, tissue perfusion imaging, or a combination thereof.

BRIEF DESCRIPTION OF THE DRAWINGS

The invention will now be described, by way of example only, with reference to the accompanying drawings, in which.

DETAILED DESCRIPTION OF THE INVENTION

Figure 1:
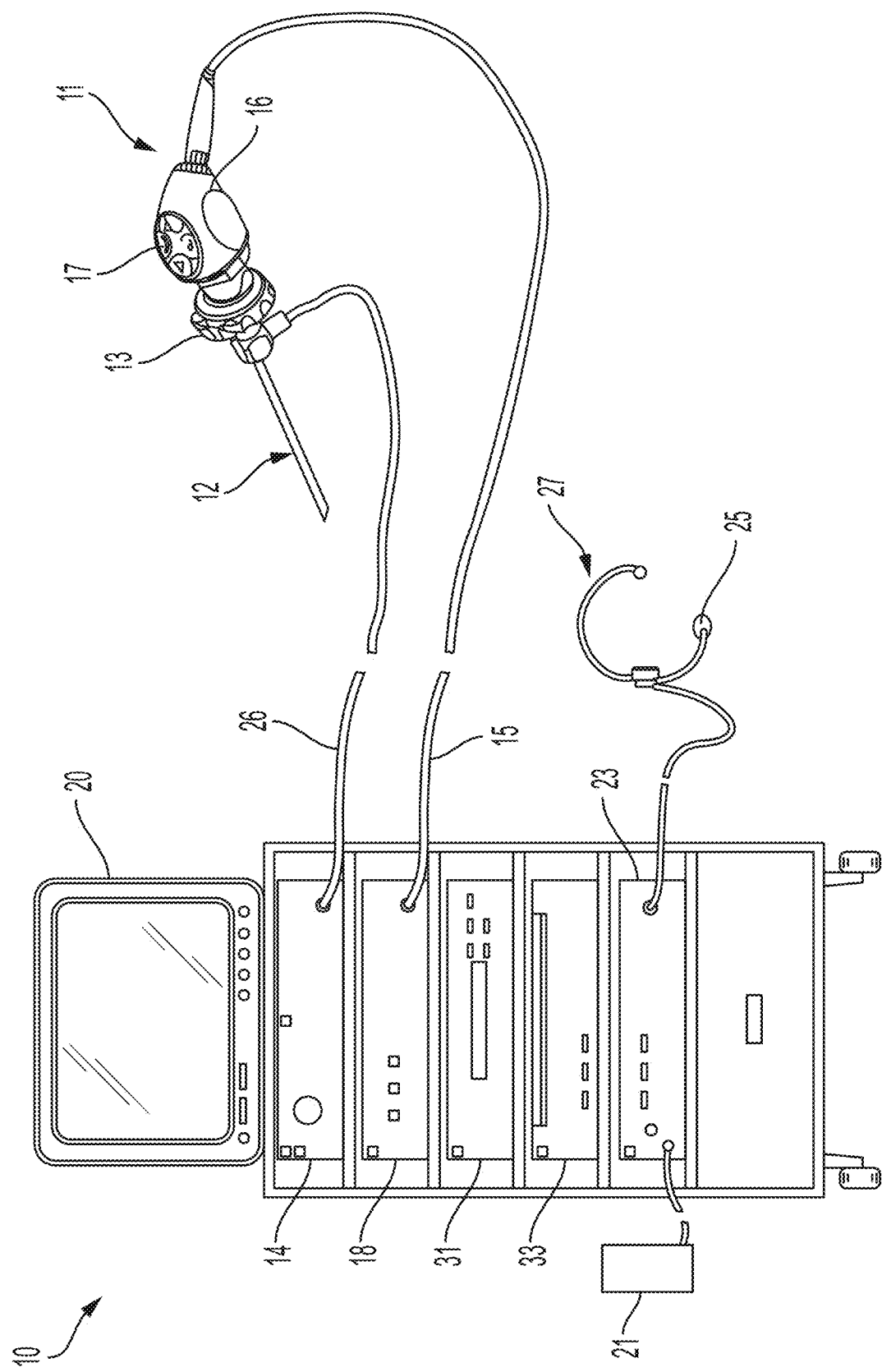
FIG. 1 is an illustration of an endoscopic camera system, according to some embodiments.

Reference will now be made in detail to implementations and embodiments of various aspects and variations of the invention, examples of which are illustrated in the accompanying drawings. Various devices, systems, methods, processors, kits and imaging agents are described herein. Although at least two variations of the devices, systems, methods, processors, kits and imaging agents are described, other variations may include aspects of the devices, systems, methods, processors, kits and imaging agents described herein combined in any suitable manner having combinations of all or some of the aspects described. Examples will now be described more fully hereinafter with reference to the accompanying drawings; however, they may be embodied in different forms and should not be construed as limited to the embodiments set forth herein. Rather, these examples are provided so that this disclosure will be thorough and complete, and will fully convey exemplary implementations to those skilled in the art.

Described herein are exemplary devices, systems, and methods for medical imaging using a rolling shutter imager and controlled illumination to generate time series of images having limited rolling shutter effects. More in general are described exemplary devices, systems, and methods for operating a rolling shutter imager and controlled illumination, such as for medical imaging, to generate time series of images having limited rolling shutter effects. The systems, devices, and methods may be used for imaging tissue of a subject, such as in endoscopic imaging procedures. Imaging may be performed pre-operatively, intra-operatively, post-operatively, and during diagnostic imaging sessions and procedures. The imaging methods per se may exclude insertion of an endoscopic imager into a lumen in the body. The imaging methods per se may exclude any invasive surgical step.

An imaging system may include a mode in which illumination to a target scene (e.g., target tissue of a patient) is controlled to produce a global shutter-type effect with a long integration time for the imaging sensor(s) pixels. An imaging sensor may be driven in accordance with a given frame rate, but instead of reading the rows of pixels of the sensor at every possible frame period, rows are read every other frame period, allowing the sensor pixels to integrate for a longer period. This results in a relatively long integration period in which substantially all rows can be simultaneously exposed to the scene. Illumination light is provided during this "global shutter" period so that the resulting image frames are substantially free of rolling shutter effects.

An imaging system may include a mode for alternately generating visible light image frames and fluorescence image frames in which illumination light is provided during an extended vertical blanking period. This mode may be used, for example, to produce white light images with fluorescence overlay. As is known in the art, a vertical blanking period in the rolling shutter imager operation is the period of time from when the last row of the sensor is reset to when the first row of the sensor is read. During the vertical blanking period, all rows are simultaneously integrating. Various embodiments achieve a global shutter-type effect by providing illumination light during the vertical blanking period. However, since the vertical blanking period is relatively short, according to some embodiments, the illumination light is provided for a longer period than the vertical blanking period to increase the sensitivity of the imager. This may result in rolling shutter effects for a portion of the rows of the sensor, and the visibility of these effects to a user may be minimized by removing or replacing one or more affected rows.

In various examples, such as those described above, the illumination light may be modulated using pulse width modulation to provide the right amount of illumination to the scene. The imaging system may control the amount of light so that the imaging sensor or sensors are optimally exposed and may do so based on intensity at the sensor(s) during one or more previous frames.

In the following description, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some embodiments also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 shows an example of an endoscopic imaging system 10, which includes a scope assembly 11 which may be utilized in endoscopic procedures. The scope assembly 11 incorporates an endoscope or scope 12 which is coupled to a camera head 16 by a coupler 13 located at the distal end of the camera head 16. Light is provided to the scope by a light source 14 via a light guide 26, such as a fiber optic cable. The camera head 16 is coupled to a camera control unit (CCU) 18 by an electrical cable 15. The CCU 18 is connected to, and communicates with, the light source 14. Operation of the camera 16 is controlled, in part, by the CCU 18. The cable 15 conveys video image and/or still image data from the camera head 16 to the CCU 18 and may convey various control signals bi-directionally between the camera head 16 and the CCU 18.

A control or switch arrangement 17 may be provided on the camera head 16 for allowing a user to manually control various functions of the system 10, which may include switch from one imaging mode to another, as discussed further below. Voice commands may be input into a microphone 25 mounted on a headset 27 worn by the practitioner and coupled to the voice-control unit 23. A hand-held control device 29, such as a tablet with a touch screen user interface or a PDA, may be coupled to the voice control unit 23 as a further control interface. In the illustrated embodiment, a recorder 31 and a printer 33 are also coupled to the CCU 18. Additional devices, such as an image capture and archiving device, may be included in the system 10 and coupled to the CCU 18. Video image data acquired by the camera head 16 and processed by the CCU 18 is converted to images, which can be displayed on a monitor 20, recorded by recorder 31, and/or used to generate static images, hard copies of which can be produced by the printer 33.

Figure 2:
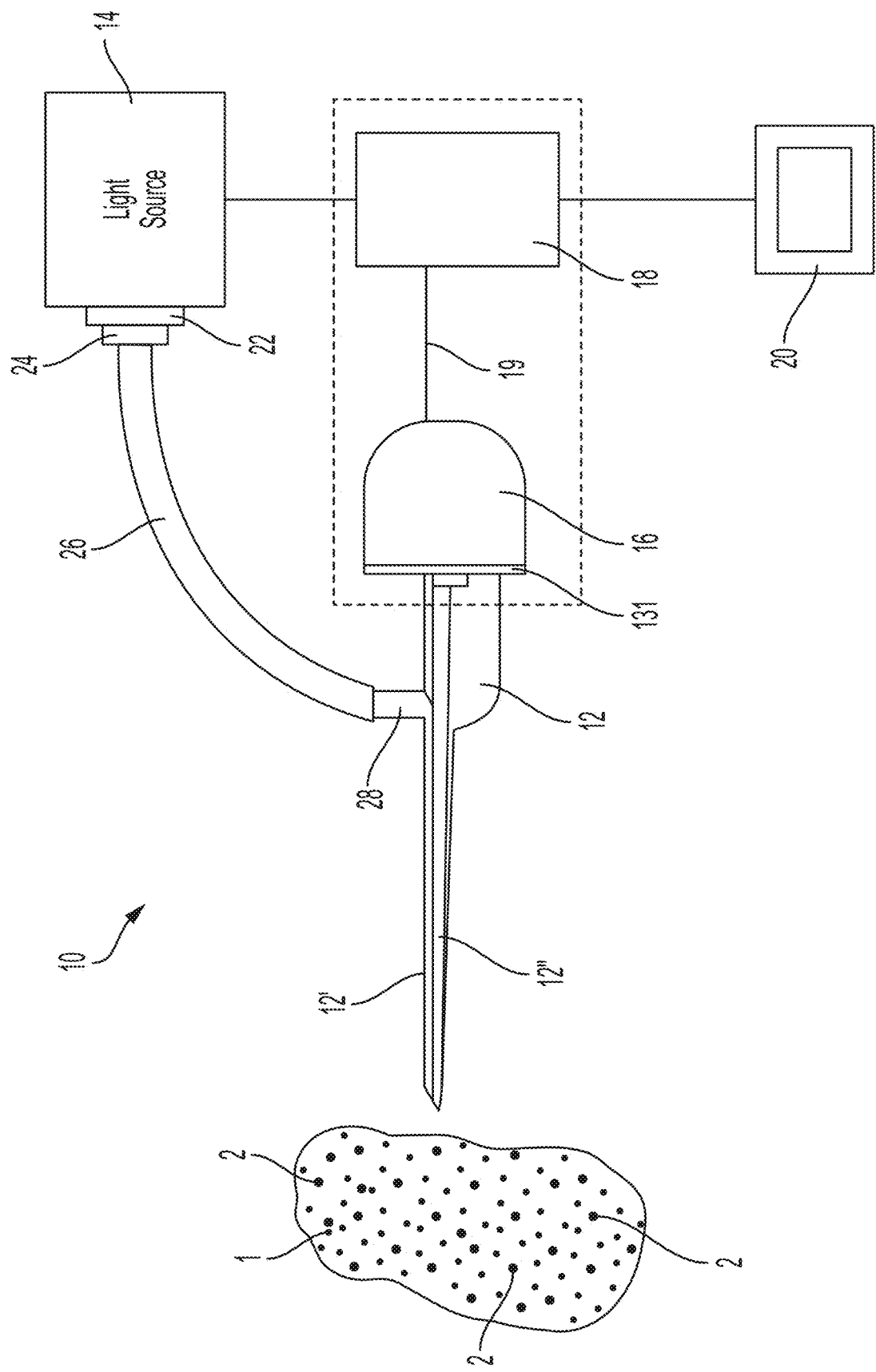
FIG. 2 is a diagram of a portion of the endoscopic camera system of FIG. 1 and an target object for imaging, according to some embodiments.

FIG. 2 shows an example of a portion of the endoscopic system 10 being used to illuminate and receive light from an object 1, such as a surgical site of a patient. The object 1 may include includes fluorescent markers 2, for example, as a result of the patient being administered a fluorescence imaging agent. The fluorescent markers 2 may be comprised of, for example, indocyanine green (ICG).

The light source 14 can generate visible illumination light (such as any combination of red, green, and blue light) for generating visible (e.g., white light) images of the target object 1 and can also produce fluorescence excitation illumination light for exciting the fluorescent markers 2 in the target object for generating fluorescence images. Illumination light is transmitted to and through an optic lens system 22 which focuses light onto a light pipe 24. The light pipe 24 may create a homogeneous light, which is then transmitted to the fiber optic light guide 26. The light guide 26 may include multiple optic fibers and is connected to a light post 28, which is part of the endoscope 12. The endoscope 12 includes an illumination pathway 12' and an optical channel pathway 12".

The endoscope 12 may include a notch filter 131 that allows some or all (preferably, at least 80%) of fluorescence emission light (e.g., in a wavelength range of 830 nm to 870 nm) emitted by fluorescence markers 2 in the target object 1 to pass therethrough and that allows some or all (preferably, at least 80%) of visible light (e.g., in the wavelength range of 400 nm to 700 nm), such as visible illumination light reflected by the target object 1, to pass therethrough, but that blocks substantially all of the fluorescence excitation light (e.g., infrared light having a wavelength of 808 nm) that is used to excite fluorescence emission from the fluorescent marker 2 in the target object 1. The notch filter 131 may have an optical density of OD5 or higher. In some embodiments, the notch filter 131 can be located in the coupler 13.

Figure 3:
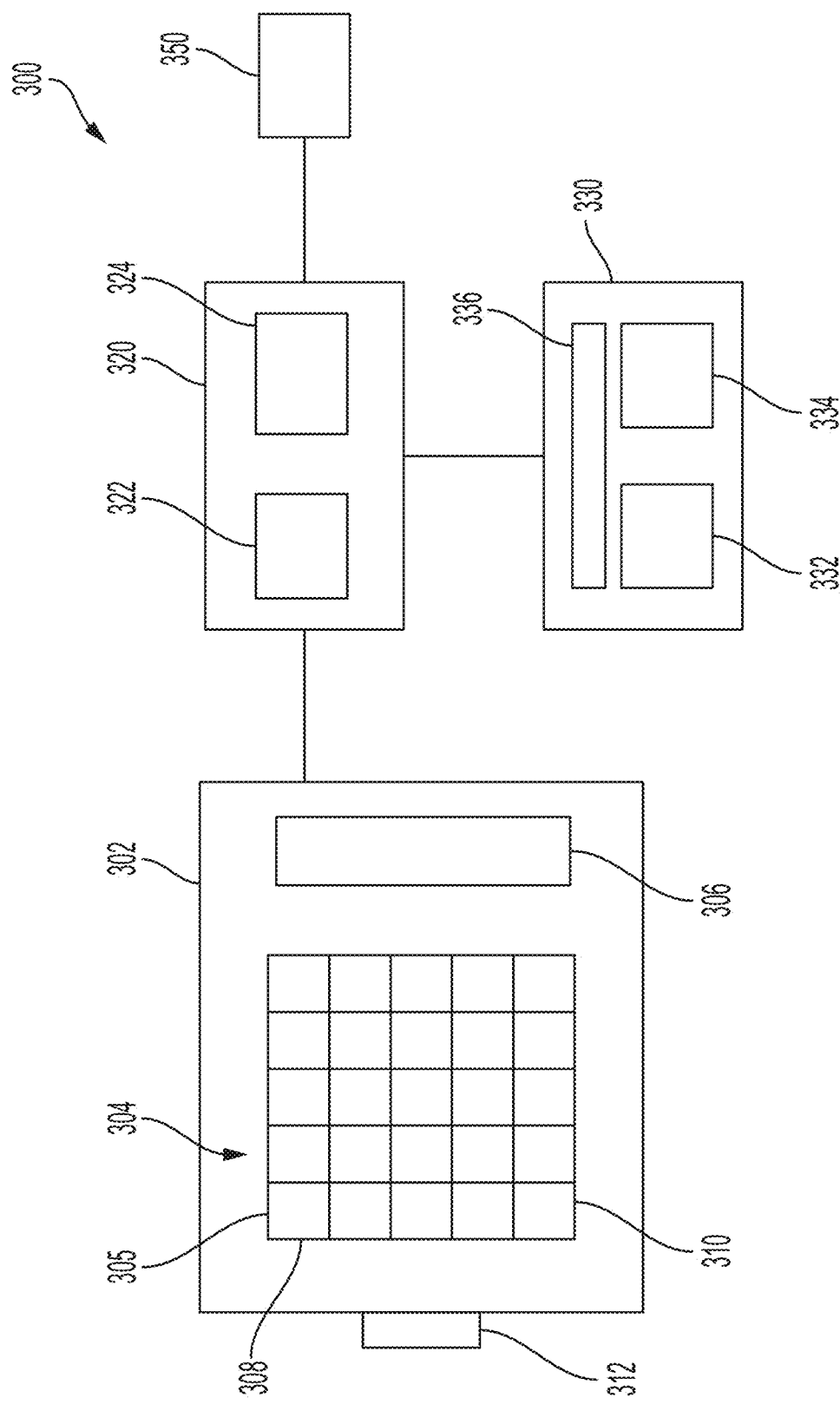
FIG. 3 is a block diagram of an imaging system, according to some embodiments.

FIG. 3 schematically illustrates an exemplary imaging system 300 that employs an electronic rolling shutter imager 302 to generate images (e.g., still and/or video) of a target object, such as a target tissue of a patient, according to some embodiments. System 300 may be used, for example, for the endoscopic imaging system 10 of FIG. 1. The imager 302 includes a CMOS sensor 304 having an array of pixels 305 arranged in rows of pixels 308 and columns of pixels 310. The imager 302 may include control components 306 that control the signals generated by the CMOS sensor 304. Example of control components include gain circuitry for generating a multi-bit signal indicative of light incident on each pixel of the sensor 304, one or more analog-to-digital converters, one or more line drivers to act as a buffer and provide driving power for the sensor 304, row circuitry, and timing circuitry. A timing circuit may include components such as a bias circuit, a clock/timing generation circuit, and/or an oscillator. Row circuitry may enable one or more processing and/or operational tasks such as addressing rows of pixels 308, addressing columns of pixels 310, resetting charge on rows of pixels 308, enabling exposure of pixels 305, decoding signals, amplifying signals, analog-to-digital signal conversion, applying timing, read out and reset signals and other suitable processes or tasks. Imager 302 may also include a mechanical shutter 312 that may be used, for example, to control exposure of the image sensor 304 and/or to control an amount of light received at the image sensor 304.

One or more control components may be integrated into the same integrated circuit in which the sensor 304 is integrated or may be discrete components. The imager 302 may be incorporated into an imaging head, such as camera head 16 of system 10.

One or more control components 306, such as row circuitry and a timing circuit, may be electrically connected to an imaging controller 320, such as camera control unit 18 of system 10. The imaging controller 320 may include one or more processors 322 and memory 324. The imaging controller 320 receives imager row readouts and may control readout timings and other imager operations, including mechanical shutter operation. The imaging controller 320 may generate image frames, such as video frames from the row and/or column readouts from the imager 302. Generated frames may be provided to a display 350 for display to a user, such as a surgeon.

The system 300 in this example includes a light source 330 for illuminating a target scene. The light source 330 is controlled by the imaging controller 320. The imaging controller 320 may determine the type of illumination provided by the light source 330 (e.g., white light, fluorescence excitation light, or both), the intensity of the illumination provided by the light source 330, and or the on/off times of illumination in synchronization with rolling shutter operation. The light source 330 may include a first light generator 332 for generating light in a first wavelength and a second light generator 334 for generating light in a second wavelength. For example, in some embodiments, the first light generator 332 is a white light generator, which may be comprised of multiple discrete light generation components (e.g., multiple LEDs of different colors), and the second light generator 334 is a fluorescence excitation light generator, such as a laser diode.

The light source 330 includes a controller 336 for controlling light output of the light generators. The controller 336 may be configured to provide pulse width modulation of the light generators for modulating intensity of light provided by the light source 330, which can be used to manage over-exposure and under-exposure. In some embodiments, nominal current and/or voltage of each light generator remains constant and the light intensity is modulated by switching the light generators (e.g., LEDs) on and off according to a pulse width control signal. In some embodiments, a PWM control signal is provided by the imaging controller 336. This control signal can be a waveform that corresponds to the desired pulse width modulated operation of light generators.

The imaging controller 320 may be configured to determine the illumination intensity required of the light source 330 and may generate a PWM signal that is communicated to the light source 330. In some embodiments, depending on the amount of light received at the sensor 304 and the integration times, the light source may be pulsed at different rates to alter the intensity of illumination light at the target scene. The imaging controller 320 may determine a required illumination light intensity for a subsequent frame based on an amount of light received at the sensor 304 in a current frame and/or one or more previous frames. In some embodiments, the imaging controller 320 is capable of controlling pixel intensities via PWM of the light source 330 (to increase/decrease the amount of light at the pixels), via operation of the mechanical shutter 312 (to increase/decrease the amount of light at the pixels), and/or via changes in gain (to increase/decrease sensitivity of the pixels to received light). In some embodiments, the imaging controller 320 primarily uses PWM of the illumination source for controlling pixel intensities while holding the shutter open (or at least not operating the shutter) and maintaining gain levels. The controller 320 may operate the shutter 312 and/or modify the gain in the event that the light intensity is at a maximum or minimum and further adjustment is needed.

Method for Generating Visible and Fluorescence Light Images

Figure 4:
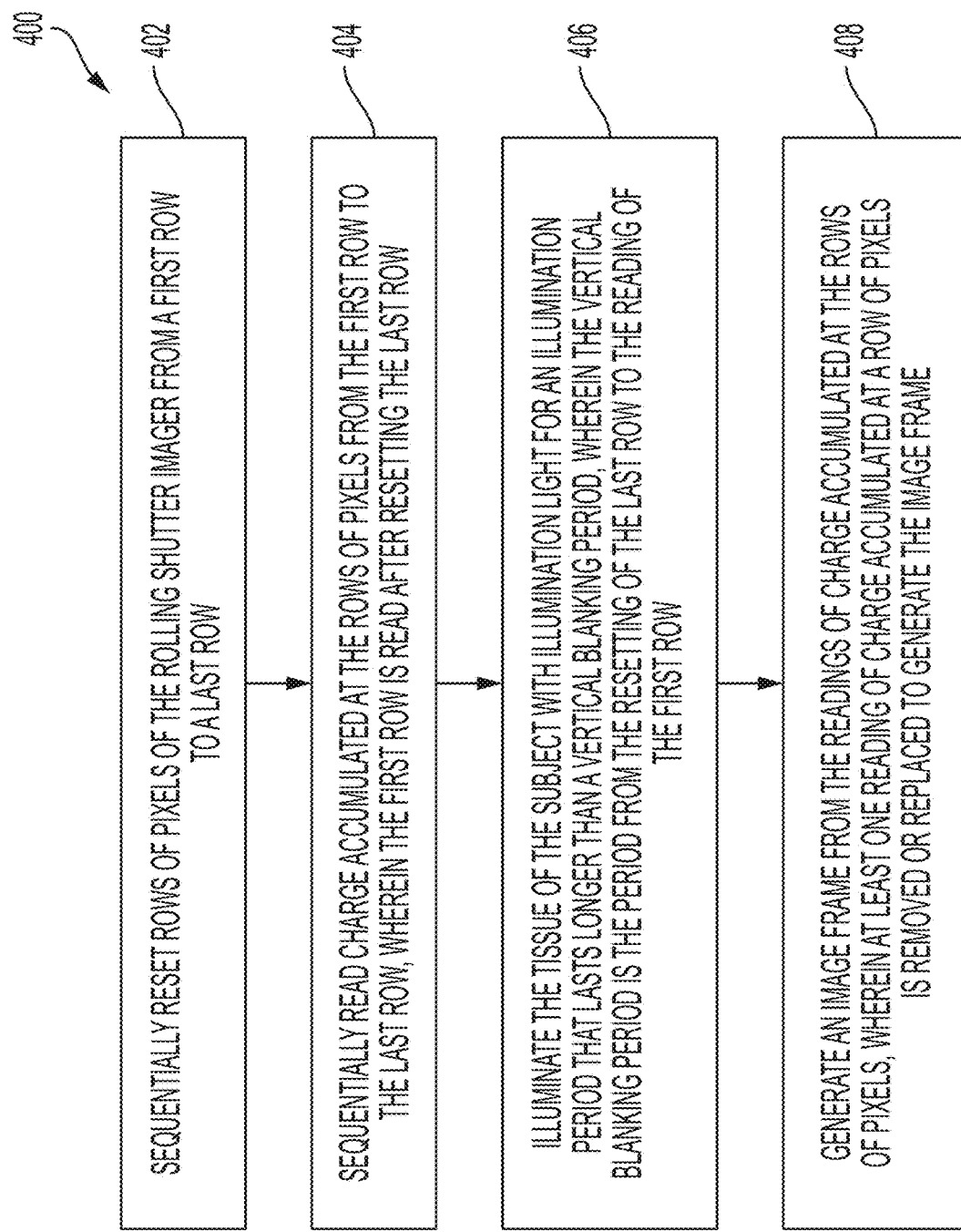
FIG. 4 is a flow diagram of a method for alternately generating white light and fluorescence image frames, according to one embodiment.

FIG. 4 illustrates an exemplary method 400 for generating time series of white light and fluorescence light image frames, according to one embodiment. Method 400 may be performed by an imaging system, such as system 300 of FIG. 3. At step 402, the rows of pixels of an electronic rolling shutter imager, such as imager 302 of FIG. 3, are sequentially reset from a first row (e.g., a top row or a bottom row) to a last row (e.g., a bottom row or a top row), according to well-known rolling shutter imager operation.

At step 404, charge accumulated at each row of pixels since the reset in step 402 is read in sequence from the first row to the last row. Reading of the first row does not begin until a period of time has elapsed since the reset of the last row in step 402. This period of time may be referred to as a vertical blanking period and is a period of time in which substantially all of the rows of the imaging sensor are simultaneously accumulating charge (i.e., integrating). This simultaneous integration period can be exploited to create a global shutter effect, as discussed further below.

At step 406, the target tissue of a subject is illuminated with illumination light from an illuminator for an illumination period. The illumination period is longer than the vertical blanking period (the time from when the last row is reset until the first row is read) and may span most or all of the vertical blanking period. The illumination period can begin prior to, at the same time as, or after the resetting of at least the last row of pixels in step 402. In any of these embodiments, the illumination period can end prior to, at the same time as, or after the reading of at least the first row of pixels in step 402.

Optionally, the illumination light may be white light (or any other visible light spectrum) for generating a white light (or any other visible light spectrum) image frame. Alternatively, or additionally, the illumination light may be fluorescence excitation light, such as infrared light, for generating a fluorescence image frame.

The length of the illumination period may be selected based on the desired imaging sensitivity for a given application. For applications with relatively higher levels of illumination light, the illumination period may be less than that for applications with relatively lower levels of illumination light. Generally, the longer the illumination period, the greater the number of rows that may be distorted, and therefore, the greater the number of rows that may need to be removed or replaced with predetermined values. Accordingly, selection of the length of the illumination period may require a balance between sensitivity and field of view.

At step 408, an image frame is generated from the readings of charge accumulated at the rows of pixels. Because the illumination period in step 406 extends beyond the vertical blanking period, not all rows are exposed to the light from the target tissue resulting from the illumination light for the same amount of time during each frame capture. For instance, in embodiments in which the illumination period begins at the resetting of the second to last row (i.e., prior to the resetting of the last row), the last row integrates light received from the target tissue due to the illumination for a shorter period of time than the previous rows. This may cause visual artifacts in the row or rows that integrate the light received due to the illumination light for a shorter period than the illumination period within each frame capture period. Accordingly, the image frame may be generated such that one or more rows affected by the extended illumination period—rows in which the illumination period begins prior to reset of the respective row and/or ends after the reading of the respective row—are removed or replaced. One or more affected rows may be replaced with one or more predetermined values. The image frame may include one or more rows in which each pixel value in a given row is the predetermined value. When displayed, the image frame may appear with, for example, one or more black lines at the top and/or bottom. In some embodiments, one or more rows affected rows are removed, such as by cropping out the affected rows. Accordingly, the generated image frame may include fewer rows than included in the pixel data from the imaging sensor.

Optionally, the method may further include alternately generating white light (or any other visible light spectrum) image frames and fluorescence image frames. At step 406 above, the illumination light may be white light and the image frame generated at step 408 may be a white light image frame. The subsequent frame capture period may be used to generate a fluorescence image frame. Accordingly, at the subsequent frame capture period, white light illumination remains off for the extended vertical blanking period. With the white light off, the illuminator generates fluorescence excitation light, such as infrared light, for causing fluorescence emission from the target tissue (e.g., due to a fluorescence agent in the tissue and/or autofluorescence of the tissue). Fluorescence emission from the target tissue is received by the rows of pixels and the readouts of the rows of pixels are used to generate a fluorescence image frame.

The subsequent frame may be used to capture a white light frame and, as such, white light illumination may be provided over a white light illumination period that spans the next vertical blanking period. This illumination period may extend into the integration period of at least some of the rows, e.g., bottom rows, for the current fluorescence image capture, and therefore, the affected rows may be replaced or removed, as discussed above.

Similarly, the illumination period from the previous white light frame (e.g., step 406 above) may extend into the integration period of at least one row of pixels during capture of the fluorescence image frame. This may cause distortion in the affected row or rows, and therefore, the affected row or rows may be removed or the associated pixel data replaced with one or more predetermined values, as discussed above.

The fluorescence excitation illumination during the fluorescence image capture period may be provided for an illumination period that spans the vertical blanking period of the frame, as discussed above with respect to the white light illumination period. The fluorescence excitation illumination period may be the same as the white light illumination period—the same duration, the same relative start time, and/or the same relative end time—or may be different.

The florescence excitation light may be provided continuously over the duration of the imaging. This may increase sensitivity to fluorescence emission from the tissue since the tissue will be emitting fluorescence light over the duration of the pixel integration period instead of just over the relatively short extended vertical blanking period. While the continuous fluorescence emission will overlap with previous and subsequent white light frame captures for at least some of the rows of pixels (due to the rolling shutter), the white light image frames may not be noticeably affected because the intensity of fluorescence emission from the tissue may be well below that of the reflected white light, such that any contribution of fluorescence emission to pixel readouts during white light frame capture may be negligible.

According to some embodiments an imager may include a mechanical shutter and the mechanical shutter may be kept open or otherwise unused for modulating light at the sensor, at least during the illumination period. Control of light intensity at the imager may be controlled, instead, via pulsing of the illumination light.

Figure 5:
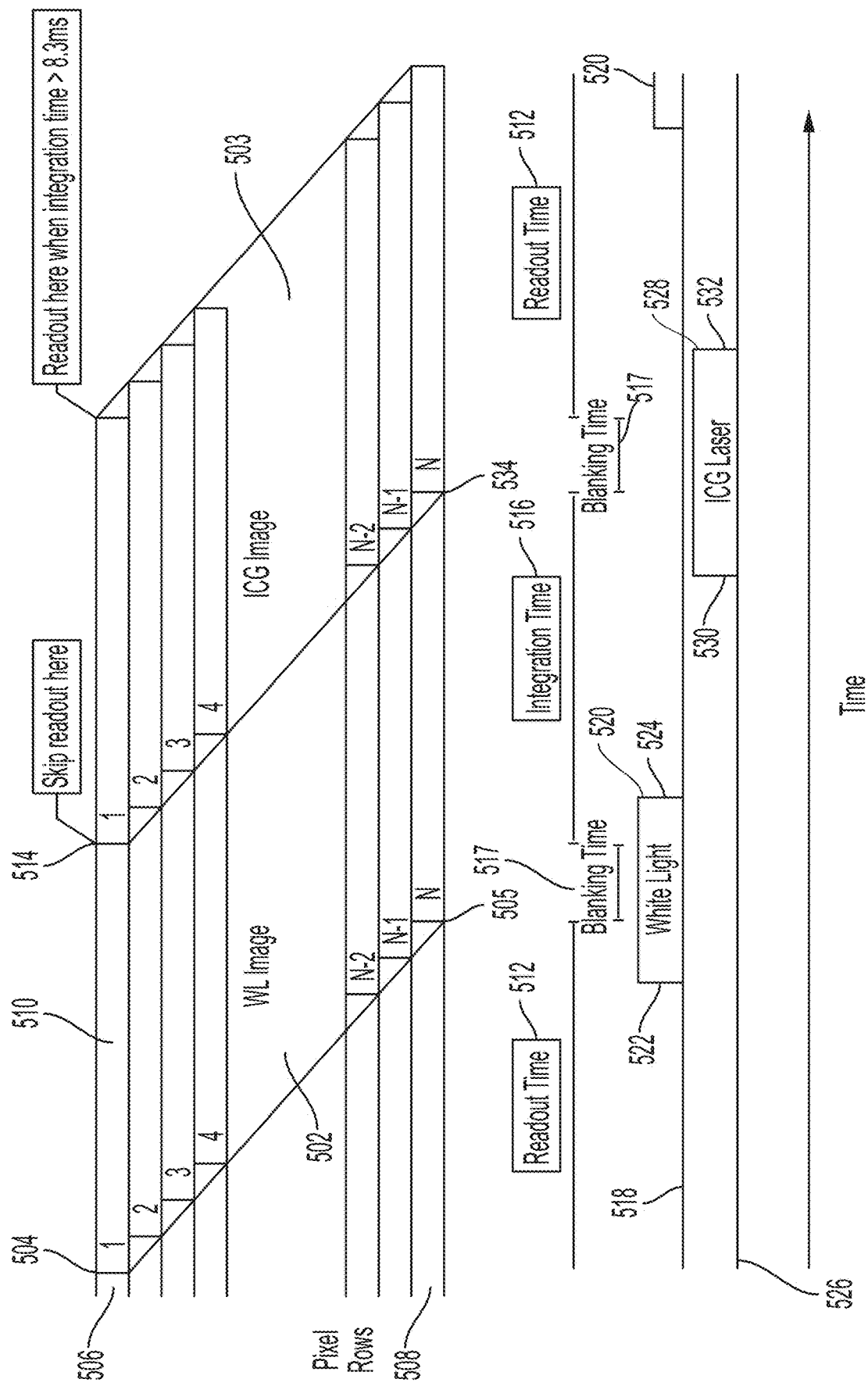
FIG. 5 is a diagram showing exemplary relative timing of imaging sensor pixel row resets and readouts and illuminator illumination for alternately generating white light and fluorescence image frames, according to one embodiment.

FIG. 5 is a diagram showing exemplary relative timing of imaging sensor pixel row resets and readouts and illuminator illumination for alternately generating white light and fluorescence image frames, according to one embodiment. The imaging sensor includes N rows, with the resets and readouts of the first four rows and the last three rows illustrated. A white light image frame capture period 502 and a subsequent fluorescence image frame capture period 503 are illustrated.

At time 504, the first row 506 is read and reset, beginning the integration period 510 for the white light image frame. Each row is read and reset is succession until the last row 508 is read and reset at time 505. The period from the first row read/reset to the last row read/reset is the readout time 512 (also referred to herein as a reset time).

At time 514, the first row 506 is read (and reset), providing intensity values for the pixels of the first row 506 associated with the amount of light received at the first row pixels during the integration period 510 of the first row 506. The readout of the first row 506 occurs after the reset of the last row 508. Each row is read (and reset) in succession until the last row 508 is read (and reset) at time 534. Each row has the same amount of integration time 516, which is shown below the rows in FIG. 5.

The period of time between the reset of the last row 508 and the readout of the first row 506 is the vertical blanking period 517. During the vertical blanking period 517, white light illumination is provided by the illuminator. An exemplary illuminator control signal 518 is shown at the bottom of FIG. 5. The illumination period 520 starts at time 522 and ends at time 524—the illuminator is not providing illumination outside of this illumination period 520 in the time frame illustrated. As can be seen, in the illustrated embodiment, the start time 522 of the white light illumination is prior to the reset of the last row 508 and the end time 524 of the illumination period 520 is after the readout time 514 of the first row 506. This extended illumination period (also referred to herein as the extended vertical blanking period, though the actual vertical blanking period is not extended) provides more time for the middle rows of pixels to accumulate charge, increasing sensitivity, than if just the illumination period 520 were restricted to just the vertical blanking period 517 alone.

The fluorescence light frame is captured in much the same way as the white light frame, as described above. In the illustration of FIG. 5, the reset of the first row for the fluorescence frame capture period 503 is depicted as the same as the readout time 514 of the first row for the white light image frame capture period 502 for simplicity sake. For the fluorescence frame, the white light control signal 518 remains low and the fluorescence excitation light signal 526 goes high, causing the illuminator to emit fluorescence excitation light. The fluorescence excitation light illumination period 528 spans the vertical blanking period 517, starting at time 530 and ending at time 532.

Since the illumination period 520 of the white light frame capture period 502 overlaps the integration period of at least the first row 506 for the fluorescence image frame capture period 503, the readout of the first row for the fluorescence frame will not be accurate with respect to the florescence response of the portion of the tissue associated with the first row 506. Accordingly, at least the readout for the first row 506 will be replaced with predetermined values, such as zeroes, or the image frame will be generated by omitting at least the first row. Further, because the subsequent image frame will be another white light image frame with a white light illumination period 520 that begins prior to the readout 536 of the last row 508 for the fluorescence image frame capture period 503, the readout 536 of the last row 508 will also not be accurate, and therefore, will be replaced or removed in generating the fluorescence image frame.

The illumination period 528 for the fluorescence image frame can be the same in length, relative start time, and/or relative end time as the illumination period 520 for the white light image frame. Alternatively, the illumination period 528 can be different than the illumination period 520, according to the relative sensitivity required for imaging the fluorescence response of the tissue versus reflected white light. In some embodiments, the fluorescence excitation is always provided, which as discussed above, may not noticeably impact the white light image capture because of the relatively low intensity of fluorescence emission from the tissue (and filtering of the fluorescence excitation light, as discussed herein).

White light image frames and fluorescence image frames are alternately generated, by repeating the above processes. The white light image frames and fluorescence image frames can be displayed separately on a display or can be displayed by, for example, overlaying the fluorescence image frame on the white light image frame. The white light frames and fluorescence frames may each be generated at half the frame rate of the imager.

According to various embodiments, the extended vertical blanking period may be selected according a balance of desired sensitivity with a desired field of view. According to various embodiments, the extended vertical blanking period may be less than twice the length of the vertical blanking period, less than three times the vertical blanking period, less than four times the vertical blanking period, less than five times the vertical blanking period, or less than ten times the vertical blanking period. According to various embodiments, the extended vertical blanking period may be at least twice the length of the vertical blanking period, at least three times the vertical blanking period, at least four times the vertical blanking period, at least five times the vertical blanking period, or at least ten times the vertical blanking period. In various embodiments, the length of the extended vertical blanking illumination period may be dynamically adjusted based on, for example, a measurement of intensity at the imaging sensor. For example, where the amount of illumination light results in relatively high light intensity at the imaging sensor for a previous frame, the illumination period may be shortened in a subsequent imaging frame. This may be done instead of or in addition to modulation of the illumination light intensity.

Optionally, the relative number of rows of pixel data that are removed or replaced due to the artifacts created by the extended vertical blanking illumination period may be less than 50%, less than 40%, less than 30%, less than 20%, less than 10%, less than 5%, less than 2%, less than 1%, less than 0.1%, less than 0.01%, less than 0.001%, or less than 0.0001%. In some embodiments, rows of pixel data of one type of imaging frame (e.g., the fluorescence imaging frame) are removed or replaced while rows of pixel data of another type of imaging frame (e.g., the white light imaging frames) are not removed or replaced. This may be useful where, for example, the fluorescence frames and white light frames are displayed on different displays or side-by-side on the same display.

Method for Generating Image Frames with Increased Sensitivity

Figure 6:
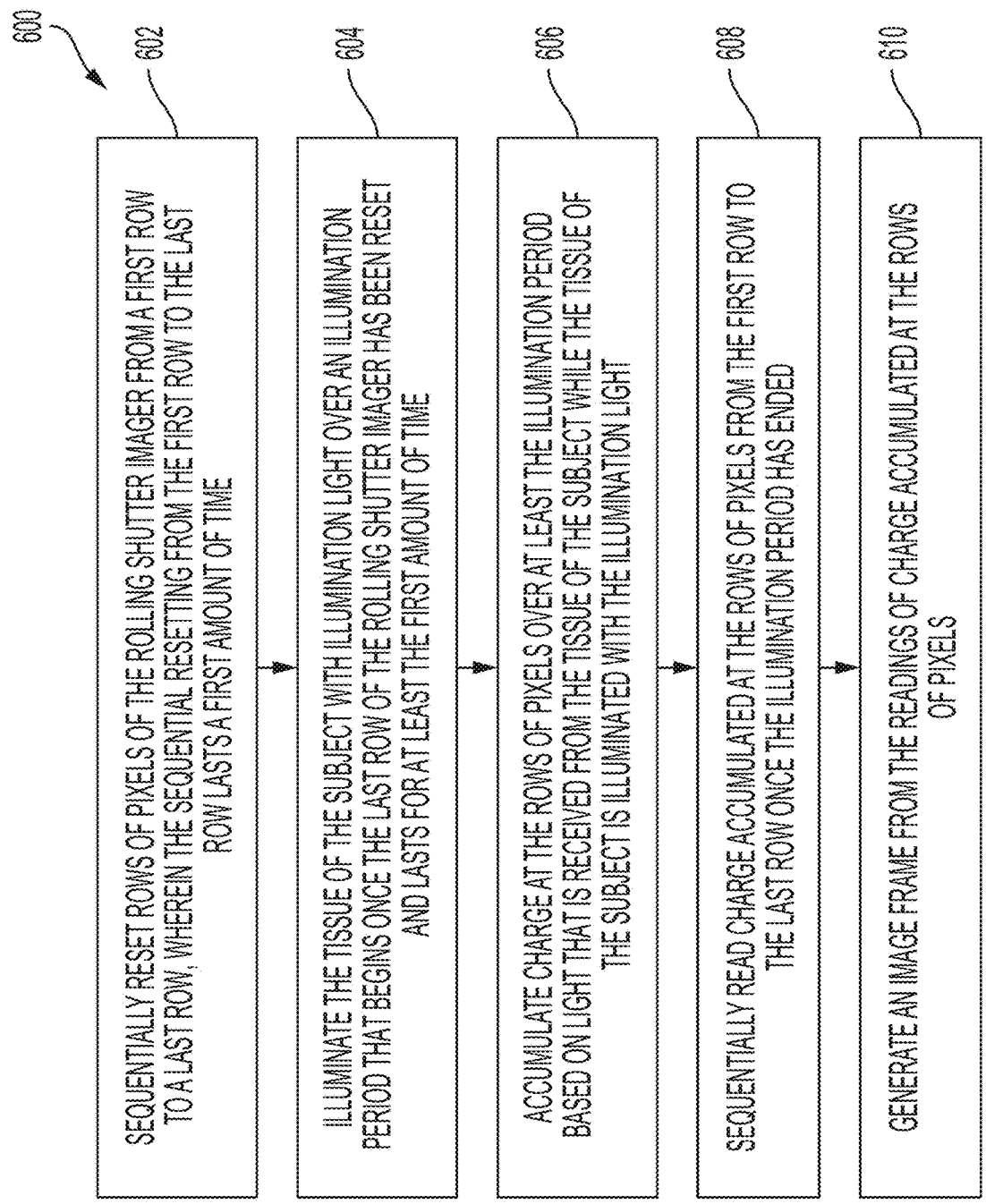
FIG. 6 is a flow diagram of a method for generating image frames with increased sensitivity by increasing the integration time, according to one embodiment.

FIG. 6 provides an exemplary method 600 for generating image frames with increased sensitivity by utilizing two frames-worth of integration time. Method 600 may be performed by an imaging system, such as imaging system 300 of FIG. 3, that has a rolling shutter imager, such as rolling shutter imager 302 of system 300, and a light source, such as light source 330 of system 300.

At step 602, the rows of pixels of the rolling shutter imager are sequentially reset from a first row to a last row, according to well-known rolling shutter imager operation. This reset (readout) period an amount of time that is referred to herein as a reset or readout period. At step 604, the target tissue of the subject is illuminated with illumination light from the illuminator over an illumination period that begins once the last row of the rolling shutter imager has been reset. The amount of time that the illumination period lasts is at least the amount of time that the reset/readout period lasts.

At step 606, charge is accumulated at the rows of pixels of the imager over at least the illumination period based on light that is received from the tissue of the subject while the tissue of the subject is illuminated with the illumination light. At step 608, the accumulated charge is read sequentially from the first row to the last row. At substantially the time that the first row is read, the illumination period has ended and the tissue is no longer illuminated with the illumination light. Thus, the tissue is illuminated in the time period between the reset of the last row and the subsequent readout of the first row. As such, each of the rows of the imager receives light from the tissue of the subject that results from the illumination of the tissue simultaneously for the same period of time, effectively creating a global shutter effect in the rolling shutter imager. This global shutter period of time is similar to the vertical blanking period discussed above with respect to method 400, but is significantly longer since it lasts at least as long as the length of the readout period.

Optionally, this global shutter period is created by skipping every other readout/reset step that the imager is capable of performing, integrating each row over two frame periods. This results in a reduction in the maximum image generation frame rate, but increases the sensitivity of the imager without introducing rolling shutter effects. In other words, the imager is driven so as to be able to produce a certain, call it nominal, frame rate (i.e., the amount of time it takes to reset/readout all lines provides the capability of achieving a nominal frame rate), but every other frame readout/reset operation is skipped, so that the image generation frame rate is half the nominal frame rate. The amount that each row is integrating while being exposed to light from the target tissue (exposure period) can be equal to twice the vertical blanking period plus the amount of time it takes to reset/readout all lines. In some embodiments, the vertical blanking period may be eliminated such that the length of the exposure period is simply the amount of time it takes to reset/readout all lines At step 610, an image frame is generated from the readings of charge accumulated at the rows of pixels. Unlike the extended illumination period of method 400, the illumination period in method 600 does not overlap with a previous and a subsequent frame. As such, no rows need be removed or replaced in generating the image frame.

The imager may include a mechanical shutter and the mechanical shutter may be kept open or otherwise unused for modulating light at the sensor, at least during the illumination period. Control of light intensity at the imager may be controlled, instead, via pulsing of the illumination light.

Figure 7:
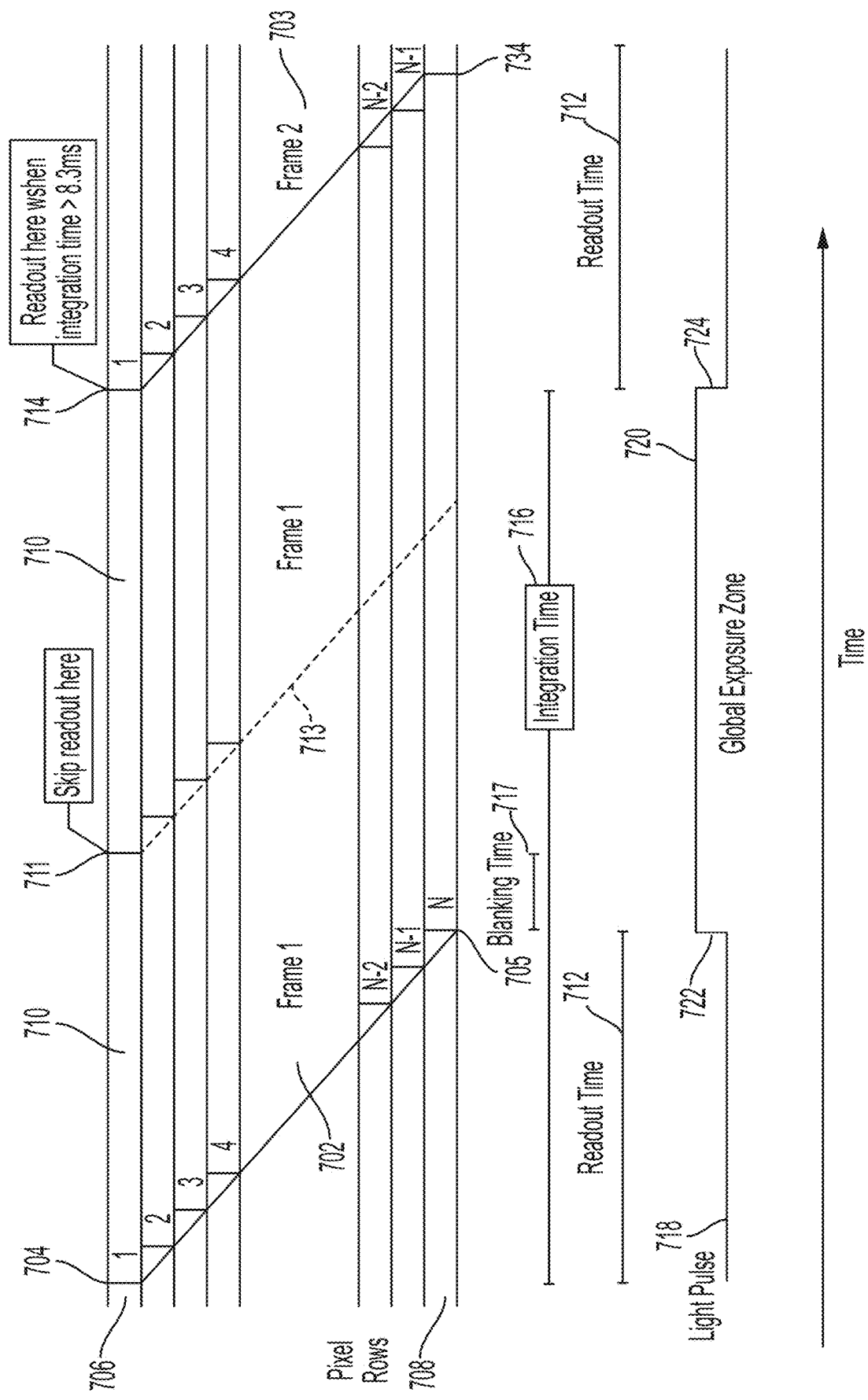
FIG. 7 is a diagram showing exemplary relative timing of imaging sensor pixel row resets and readouts and illuminator illumination for generating image frames with increased sensitivity, according to one embodiment.

FIG. 7 is a diagram showing exemplary relative timing of imaging sensor pixel row resets and readouts and illuminator illumination for generating image frames with increased sensitivity, according to one embodiment. The imaging sensor includes N rows, with the resets and readouts of the first four rows and the last three rows illustrated. An image frame capture period 702 and the very beginning of a subsequent image frame capture period 703 are illustrated.

At time 704, the first row 706 is read and reset, beginning the integration period 710 for the image frame. Each row is read and reset is succession until the last row 708 is read and reset at time 705. The period from the first row read/reset to the last row read/reset is the readout time 712 (also referred to herein as a reset time).

At time 711, the reset period and the vertical blanking period 717 have completed, and therefore, the imager is capable of another reset/readout operation. However, this step is skipped so that the integration period for each row is longer. This readout/reset capability is represented by the dashed line 713. At time 714, the first row 706 is read (and reset), providing intensity values for the pixels of the first row 706 associated with the amount of light received at the first row pixels during the integration period 710 of the first row 706. The readout of the first row 706 occurs well after (relatively) the reset of the last row 508. Each row is read (and reset) in succession until the last row 708 is read (and reset) and time 734. Each row has the same amount of integration time 716. Due to skipping the readout/reset at time 714, the integration period for each row may be effectively doubled.

In the illustrated example, the period of time between the reset of the last row 708 and the readout of the first row 706 is equal to the readout time plus double the vertical blanking period 717. During this time, substantially all of the rows of the imager are simultaneously exposed, effectively creating a global shutter window in which illumination light can be provided such that rolling shutter effects are prevented. In the exemplary embodiment, the illumination light is provided during the entirety of this global shutter window. An exemplary illuminator control signal 718 is shown at the bottom of FIG. 7. The illumination period 720 start time 722 may be the same as the readout/reset time 705 for the last row 708. The illumination period 720 end time 724 may be the same as the readout/reset time 714 for the first row 706. The illuminator is off outside of this illumination window. The illumination period can be shorter than the global shutter period—it can start at some time after the reading of the last row and/or can end prior to the readout of the first row.

According to some embodiments, an imager may be configured for any suitable frame rate. Exemplary frame rates include at least 30 fps, at least 60 fps, at least 120 fps, and at least 240 fps. Global shutter window times and/or extended vertical blanking times are generally related to the frame rate capability of the imager, whereby faster frame rates will be associated with shorter global shutter window times and/or shorter extended vertical blanking times.

Illuminator for Pulse Width Modulated Illumination

An imaging system, such as imaging system 300 of FIG. 3, may be configured to modulate the amount of illumination light provided to the target object (e.g., target tissue) by pulsing the illumination light sources of the illuminator, as discussed above. The amount of illumination light may be modulated so that the amount of reflected light (or fluorescence emission light) received at the imaging sensor can be controlled. Pulse width modulation (PWM) allows the amount of light received at the target object to be rapidly changed so that the amount of light received at the imager can be adjusted rapidly, such as for every imaging frame. In some embodiments, PWM of the light source can replace other means of modulating light intensity at the imaging sensor, such as a mechanical shutter. In some embodiments, PWM of the light source may provide a primary mechanism for adjusting light at the sensor and a mechanical shutter may provide a secondary mechanism should adjustment of the light source be insufficient. The imager may also rely upon gain adjustments in addition to illuminator PWM adjustments during image frame generation.

Figure 8:
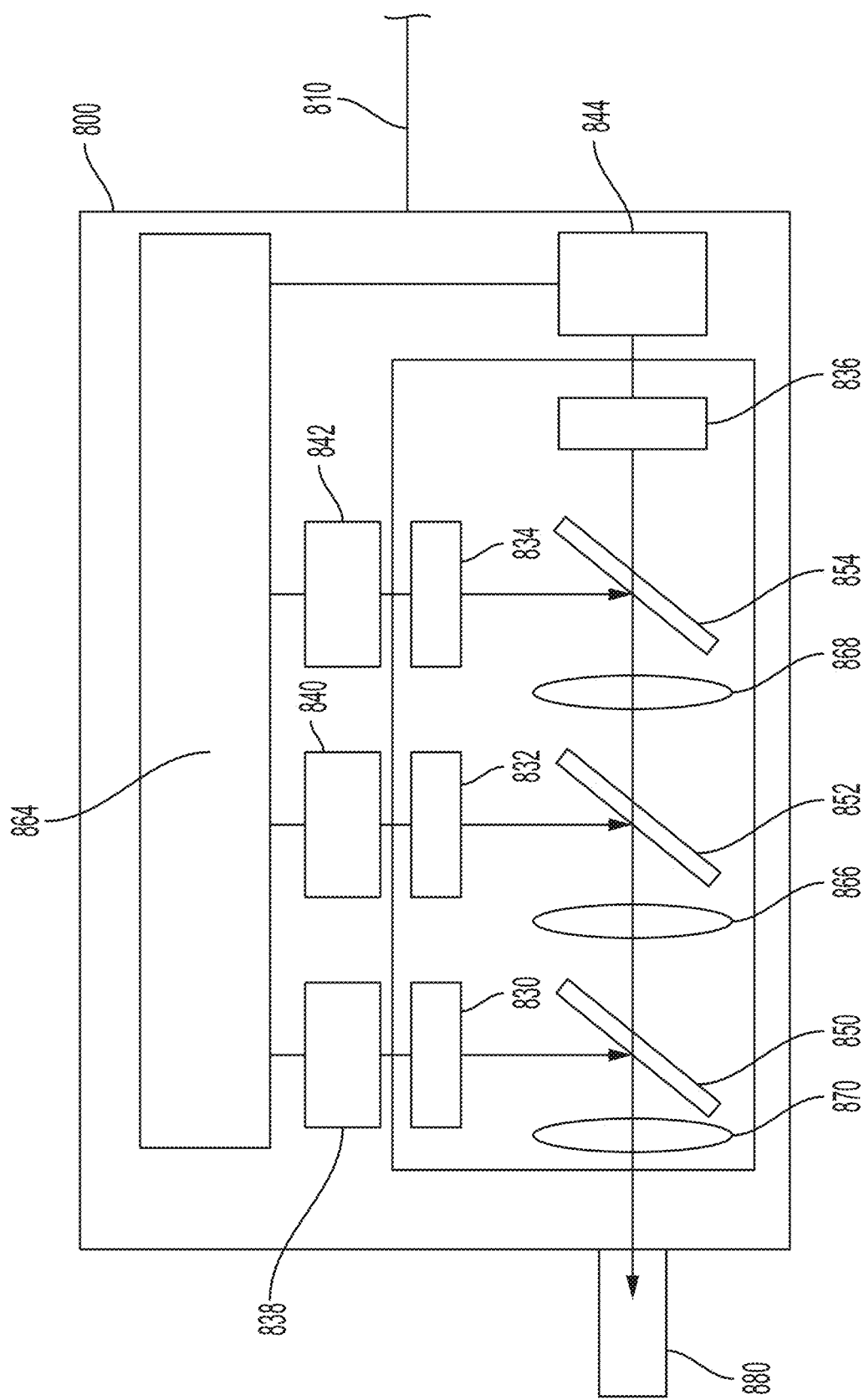
FIG. 8 is a blocking diagram illustrating components of an exemplary illuminator that may be used for generating pulse width modulated illumination light, according to some embodiments.

FIG. 8 is a blocking diagram illustrating components of an exemplary illuminator 800 that may be used for generating pulse width modulated illumination light, according to one embodiment. Illuminator 800 may be configured for generating white light as well as fluorescence excitation light, such as infrared light. The illuminator 800 includes a laser diode 830, a first LED 832, a second LED 834, and a third LED 836. The laser diode 830 may be for providing fluorescence excitation light and the three LEDs may be for providing visible light, such as red, green, and blue light, and any combination thereof (e.g., white light). The laser diode 830 is activated by a laser diode driver 838. The first LED 832 is activated by a first LED driver 840, the second LED 834 is activated by a second LED driver 842, and the third LED 836 is activated by a third LED driver 844.

In some embodiments, the laser diode 830 is an infrared diode that emits light having a wavelength in the range of about 805 nm to about 810 nm. In some embodiments, the laser diode emits light having a wavelength of about 808 nm. Preferably, the first LED 832 emits light in the blue wavelength spectrum, the second LED 834 emits light in the green wavelength spectrum, and the third LED 836 emits light in the red wavelength spectrum.

In front of the laser diode 830 is a first dichroic filter 850, in front of the first LED 832 is a second dichroic filter 852, and in front of both the second LED 834 and the third LED 836 is a third dichroic filter 854. The dichroic filters 850, 852, 854 are each designed to reflect certain light and allow passage of other light therethrough. The first dichroic filter 850 allows the light from all three LEDs 832, 834, and 836 (e.g., light in the blue, green, and red wavelength spectra) to pass, while reflecting the laser light from the laser diode 830. The second dichroic filter 852 allows light from the second and third LEDs 834, 836 to pass while reflecting light from the first LED 832. The third dichroic filter 854 allows light from the third LED 836 to pass, while reflecting light from the second LED 834.

A first optical lens 866 is located between the first dichroic filter 850 and the second dichroic filter 852 for focusing light received from the second dichroic filter 852 to be passed to the first dichroic filter 850. A second optical lens 868 is located between the second dichroic filter 852 and the third dichroic filter 854, and is for focusing light received from the third dichroic filter 854 to be passed to the second dichroic filter 852. A third optical lens 870 may be provided for focusing light received from the first dichroic filter 850. Light may be provided by the illuminator 800 via a light transmission line 880, such as a fiber optic light pipe.

A controller 864 is provided for activating and modulating the illumination sources according to various modes and control signals that may be received from, for example, a camera control unit via control line 810. An exemplary illumination mode, according to various embodiments, can include a visible white light mode in which the laser diode 830 is off, the first LED 832 is on, the second LED 834 is on, and the third LED 836 is on. This mode can be used, for example, in the method 600 of FIG. 6, as described above.

Another exemplary illumination mode is an alternating infrared excitation light and white light mode that can be used, for example, in alternately generating white light and fluorescence light image frames, such as in method 400 of FIG. 4. In this mode, the first LED 832, second LED 834, and third LED 836 are on simultaneously periodically and the laser diode 830 is on all of the time or periodically.

The switching from mode to mode, such as from a white light mode to white light plus fluorescence light illumination mode in both the illuminator 800 and the imager can be achieved by use of camera head buttons, a CCU touch screen, a light source touch screen, a wireless controller touch screen, a voice control, a foot pedal, or any other suitable mechanism.

The controller 864 may be configured to control pulsing of the individual light sources in the illuminator 800. The controller 864 may provide pulsing control signals to the illumination source drivers that cause the drivers to activate and deactivate the light sources according to the desired pulse width modulation. In some embodiments, the controller 864 receives a PWM signal from an external control system, such as a camera control system, over control line 810 and uses the PWM signal to pulse the light sources. In other words, a waveform that corresponds to the desired PWM of the light sources may be provided to the illuminator 800 over control line 810 and this PWM waveform may be provided to the drivers via the controller without any software-based processing of the PWM signal. In other embodiments, the controller 864 receives a control signal from an external control system generates its own PWM signal according to the received control signal. For example, an external controller, such as a CCU, may provide a relative intensity control parameter, and the controller 864 may generate a PWM signal according to the intensity control parameter.

Exemplary Imager

Figure 9:
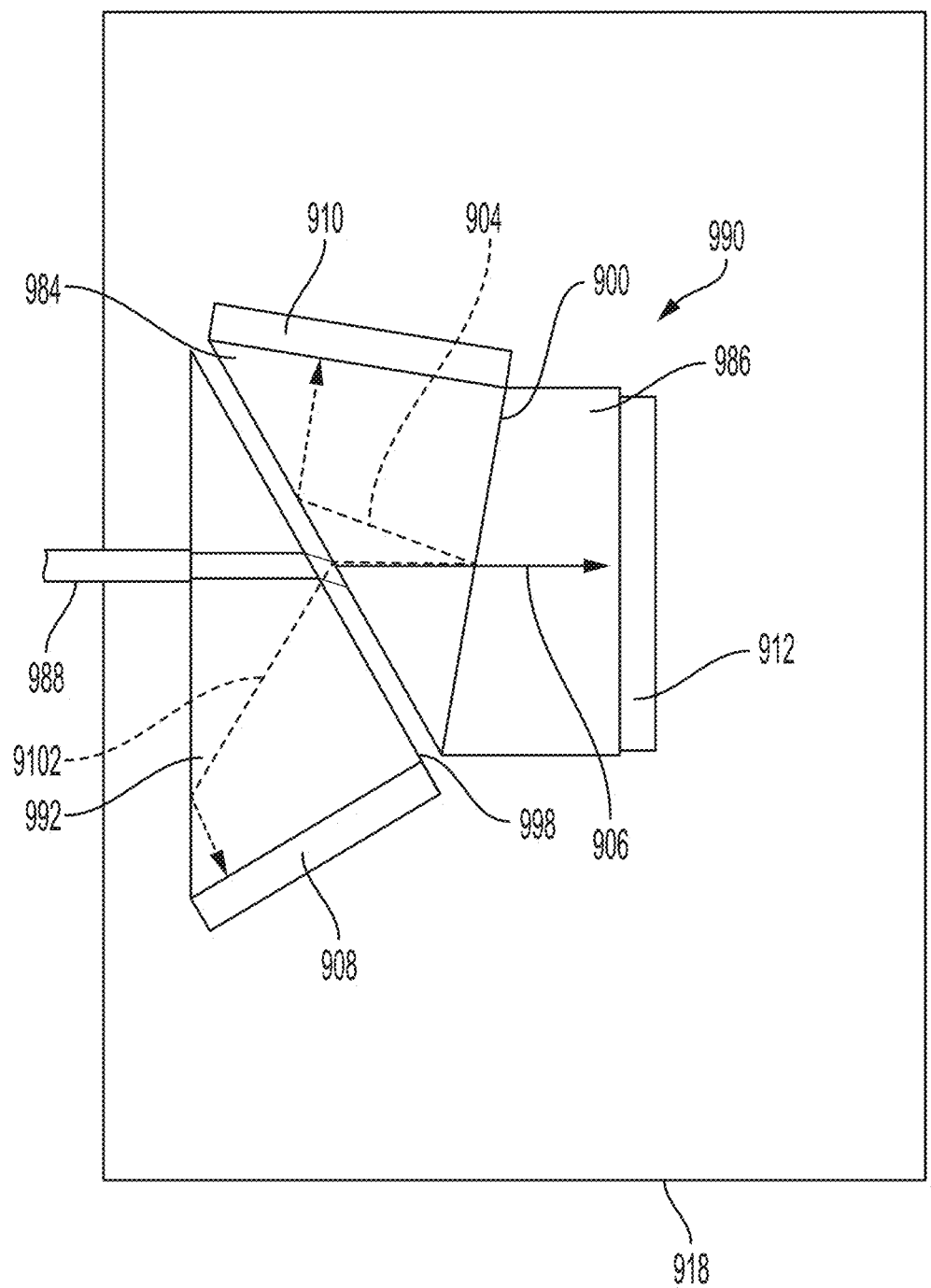
FIG. 9 is a diagrammatic illustration of an imager having three imaging sensors, according to some embodiments.

FIG. 9 illustrates an exemplary rolling shutter imager 916 that include three imaging sensors. The imager 916 may be used as or in camera head 16 of system 10 of FIG. 1 or as imager 302 of system 300. Light reaches the imager via path 988. The imager 916 includes, among other components not shown, a trichroic prism 990. The trichroic prism 990 includes a first glass prism 992, a second glass prism 994, and a third glass prism 996. Between the first glass prism 992 and the second glass prism 994 is a first prism filter 998, which may be in the form of a coating on the exterior of the first glass prism 992. The first prism filter 998 reflects blue light, but transmits other light, such as red light, green light, and infrared light. Between the second glass prism 994 and the third glass prism 996 is a second prism filter 900, which may be in the form of a coating on the second glass prism 994. The second prism filter 900 reflects red light and infrared light, but allows the transmission of light in other wavelengths, such as green light. Thus, blue light is transmitted along the pathway 902, red and infrared light are transmitted along the pathway 904, and green light is transmitted along the pathway 906.

A first color sensor 908 is adjacent, and preferably fixedly attached to, the first glass prism 992. A second color sensor 910 is adjacent, and preferably fixedly attached to, the second glass prism 994. A third color sensor 912 is adjacent, and preferably fixedly attached to, the third glass prism 996. The first color sensor 908 is capable of detecting light in the blue wavelength spectrum, the second color sensor 910 is capable of detecting light in the red and infrared wavelength spectra, and the third color sensor 912 is capable of detecting light in the green wavelength spectrum. The color sensors 908, 910, 912 are rolling shutter imagers, such as CMOS imagers, that receive light and convert the light into electronic signals, which in turn are transmitted to a processor (e.g., CCU 18 of system 10) for processing into analog or digital signals of images to be provided for display, such as to monitor 20 of system 10.

Figure 10:
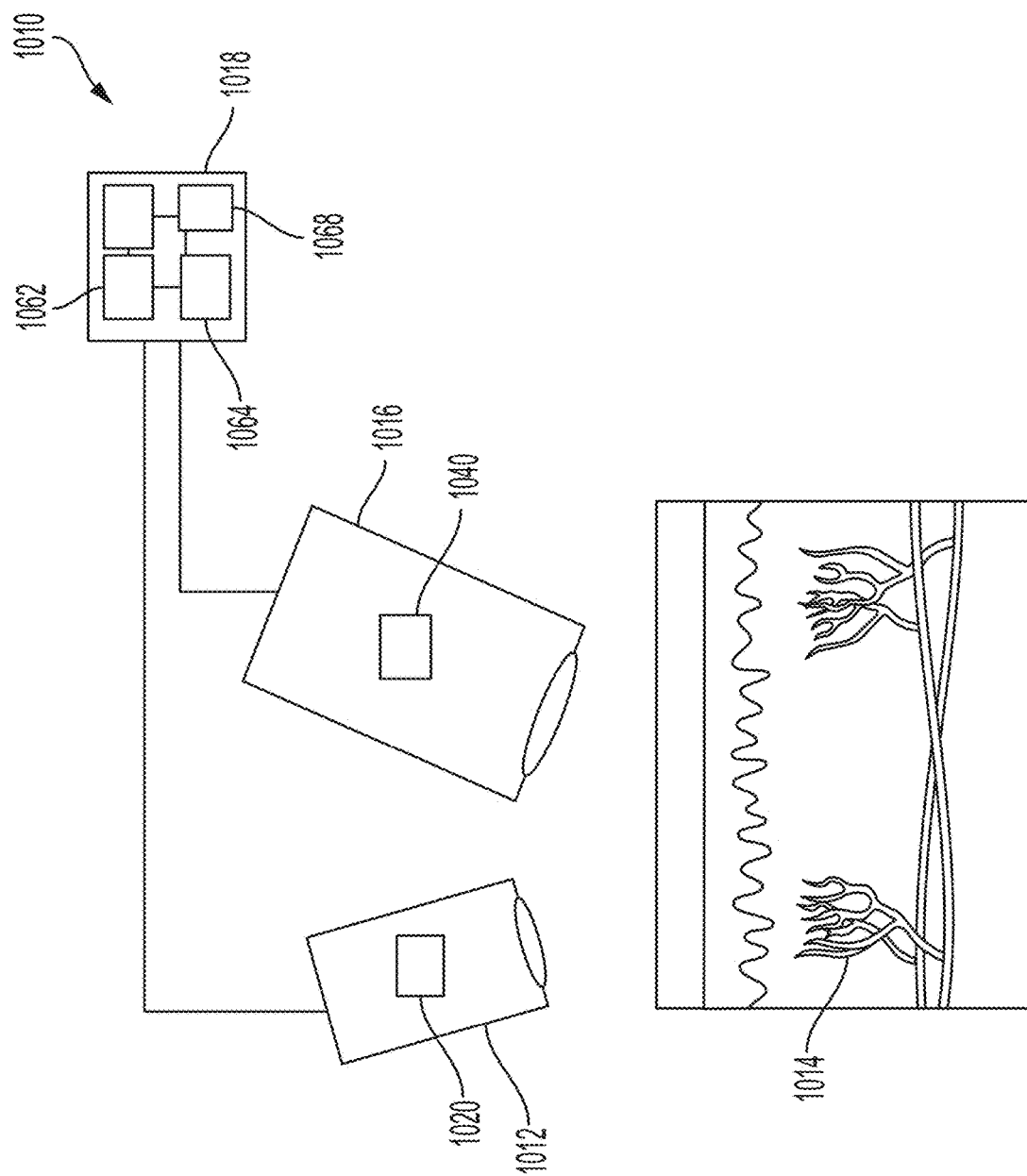
FIG. 10 is an illustrative depiction of an exemplary fluorescence imaging system, according to some embodiments.

Optionally, an imaging system is a fluorescence imaging system. FIG. 10 is a schematic example of a fluorescence imaging system 1010. The fluorescence imaging system 1010 comprises a light source 1012 to illuminate the tissue of the subject to induce fluorescence emission from a fluorescence imaging agent 1014 in the tissue of the subject (e.g., in blood, in urine, in lymph fluid, in spinal fluid or other body fluids or tissues), an image acquisition assembly 1016 arranged for generating the time series and/or the subject time series of fluorescence images from the fluorescence emission, and a processor assembly 1018 arranged for processing the generated time series/subject time series of fluorescence images according to any of the variations of the methods described herein. The processor assembly 1018 may include memory 1068 with instructions thereon, a processor module 1062 arranged for executing the instructions on memory 1068 to process the time series and/or subject time series of fluorescence images, and a data storage module 1064 to store the unprocessed and/or processed time series and/or subject time series of fluorescence images. In some variations, the memory 1068 and data storage module 1064 may be embodied in the same storage medium, while in other variations the memory 1068 and the data storage module 1064 may be embodied in different storage mediums. The system 1010 may further include a communication module 1066 for transmitting images and other data, such as some or all of the time series/subject time series of fluorescence images or other input data, spatial maps, subject spatial maps, and/or a tissue numerical value (quantifier), to an imaging data processing hub.

Figure 11:
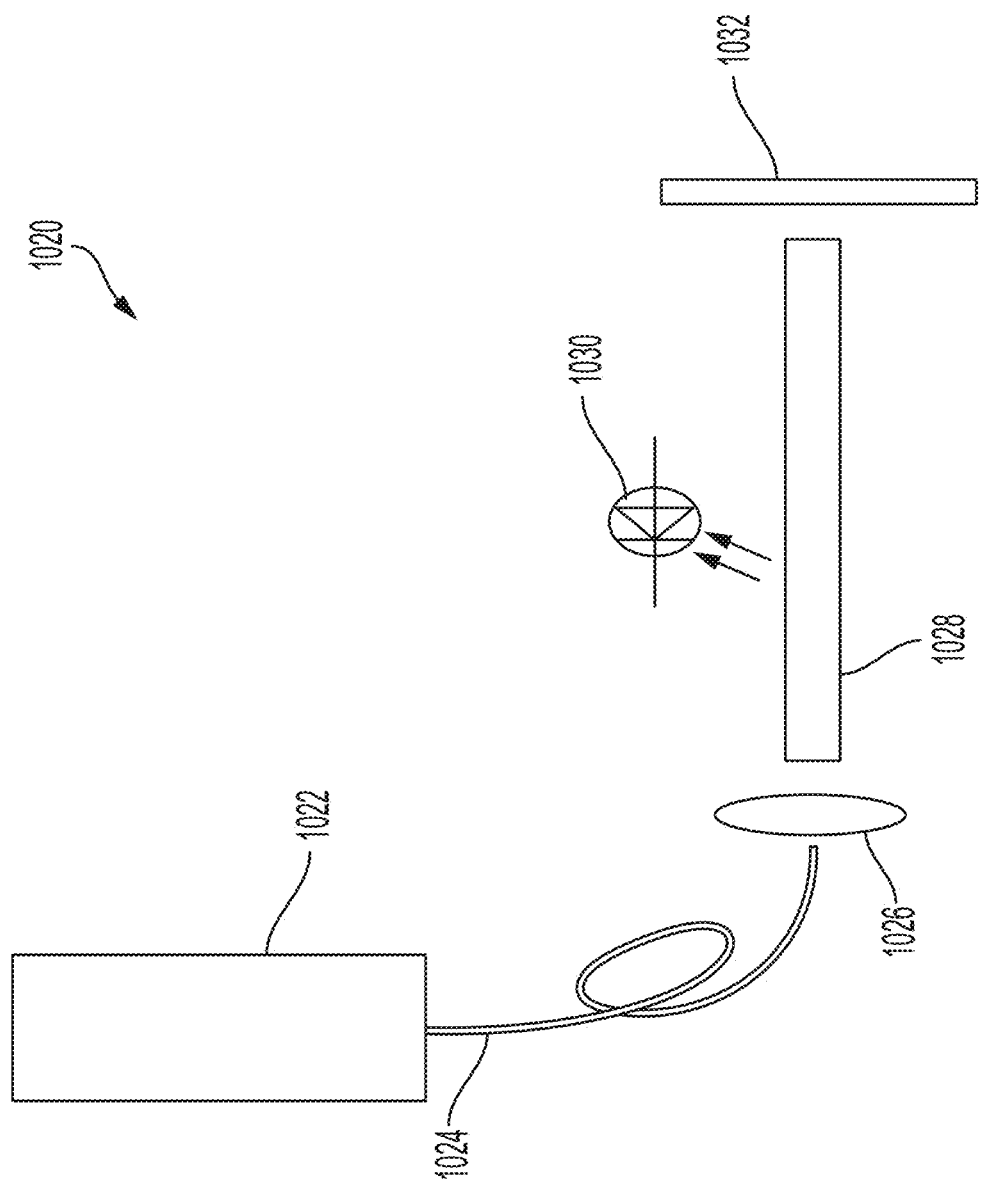
FIG. 11 is an illustrative depiction of an exemplary illumination module of a fluorescence imaging system, according to some embodiments.

In some variations, the light source 1012 includes, for example, an illumination module 1020. Illumination module 1020 may include a fluorescence excitation source arranged for generating an excitation light having a suitable intensity and a suitable wavelength for exciting the fluorescence imaging agent 1014. As shown in FIG. 11, the illumination module 1020 may comprise a laser diode 1022 (e.g., which may comprise, for example, one or more fiber-coupled diode lasers) arranged for providing an excitation light to excite the fluorescence imaging agent (not shown) in tissue of the subject. Examples of other sources of the excitation light which may be used in various embodiments include one or more LEDs, arc lamps, or other illuminant technologies of sufficient intensity and appropriate wavelength to excite the fluorescence imaging agent in the tissue. For example, excitation of the fluorescence imaging agent in blood, wherein the fluorescence imaging agent is a fluorescence dye with near infra-red excitation and emission characteristics, may be performed using one or more 793 nm, conduction-cooled, single bar, fiber-coupled laser diode modules from DILAS Diode Laser Co, Germany.

In some variations, the light output from the light source 1012 may be projected through one or more optical elements to shape and guide the output being used to illuminate the tissue area of interest. The optical elements may include one or more lenses, light guides, and/or diffractive elements so as to ensure a flat field over substantially the entire field of view of the image acquisition assembly 1016. The fluorescence excitation source may be selected to emit at a wavelength close to the absorption maximum of the fluorescence imaging agent 1014 (e.g., indocyanine green (ICG), etc.). For example, as shown in FIG. 11, the output 1024 from the laser diode 1022 may be passed through one or more focusing lenses 1026, and then through a homogenizing light pipe 1028 such as, for example, light pipes commonly available from Newport Corporation, USA. Finally, the light may be passed through an optical diffractive element 1032 (i.e., one or more optical diffusers) such as, for example, ground glass diffractive elements also available from Newport Corporation, USA. Power to the laser diode 1022 may be provided by, for example, a high-current laser driver such as those available from Lumina Power Inc. USA. The laser may optionally be operated in a pulsed mode during the image acquisition process. An optical sensor such as a solid state photodiode 1030 may be incorporated into the illumination module 1020 and may sample the illumination intensity produced by the illumination module 1020 via scattered or diffuse reflections from the various optical elements. In some variations, additional illumination sources may be used to provide guidance when aligning and positioning the module over the area of interest.

Figure 12:
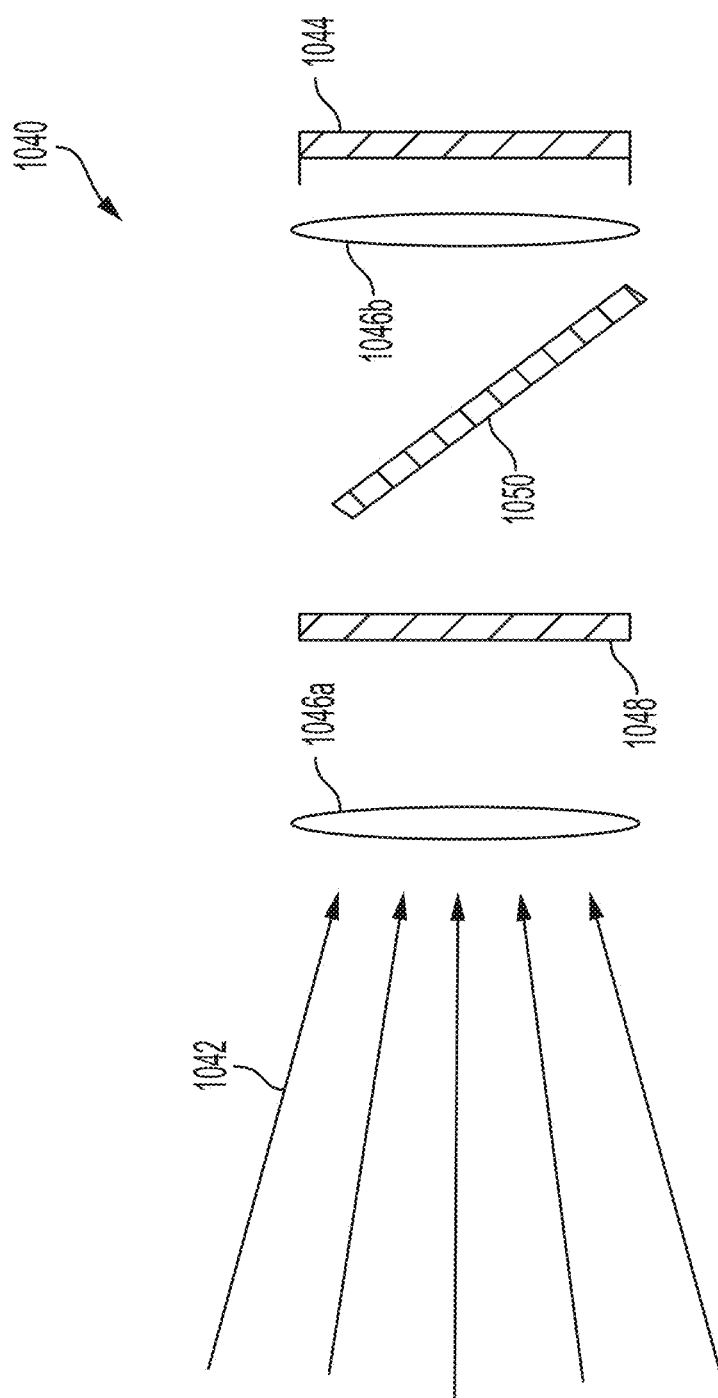
FIG. 12 is an exemplary camera module of a fluorescence imaging system, according to some embodiments.

Referring again to FIG. 10, in some variations, the image acquisition assembly 1016 may be a component of a fluorescence imaging system 1010 configured to acquire the time series and/or subject time series of fluorescence images from the fluorescence emission from the fluorescence imaging agent 1014. The image acquisition assembly 1016 may include a camera module 1040. As shown in FIG. 12, the camera module 1040 may acquire images of the fluorescence emission 1042 from the fluorescence imaging agent in the tissue by using a system of imaging optics (e.g., 1046a, 1046b, 1048 and 1050) to collect and focus the fluorescence emission onto an image sensor assembly 1044. The image sensor assembly 1044 may comprise at least one 2D solid state image sensor. The solid state image sensor may be a charge coupled device (CCD), a CMOS sensor, a CID or similar 2D sensor technology. The charge that results from the optical signal transduced by the image sensor assembly 1044 is converted to an electrical video signal, which includes both digital and analog video signals, by the appropriate read-out and amplification electronics in the camera module 1040.

According to an exemplary variation of a fluorescent imaging system, the light source may provide an excitation wavelength of about 800 nm+/−10 nm, and the image acquisition assembly uses emission wavelengths of >820 nm with NIR-compatible optics for, for example, ICG fluorescence imaging. In an exemplary embodiment, the NIR-compatible optics may include a CCD monochrome image sensor having a GigE standard interface and a lens that is compatible with the sensor with respect to optical format and mount format (e.g., C/CS mount).

In some variations, the processor module 1062 comprises any computer or computing means such as, for example, a tablet, laptop, desktop, networked computer, or dedicated standalone microprocessor. For instance, the processor module 1062 may include one or more central processing units (CPU). In an exemplary embodiment, the processor module 1062 is a quad-core, 2.5 GHz processor with four CPUs where each CPU is a microprocessor such as a 64-bit microprocessor (e.g., marketed as INTEL Core i3, i5, or i7, or in the AMD Core FX series). However, in other embodiments, the processor module 1062 may be any suitable processor with any suitable number of CPUs and/or other suitable clock speed.

Inputs for the processor module 1062 may be taken, for example, from the image sensor 1044 of the camera module 1040 shown in FIG. 12, from the solid state photodiode 1030 in the illumination module 1020 in FIG. 11, and/or from any external control hardware such as a footswitch or remote-control. Output is provided to the laser diode driver and optical alignment aids. As shown in FIG. 10, in some variations, the processor assembly 1018 may have a data storage module 1064 with the capability to save the time series/subject time series of images, or data representative thereof, or other input data to a tangible non-transitory computer readable medium such as, for example, internal memory (e.g. a hard disk or flash memory), so as to enable recording and processing of acquired data. In some variations, the processor module 1062 may have an internal clock to enable control of the various elements and ensure correct timing of illumination and sensor shutters. In some variations, the processor module 1062 may also provide user input and graphical display of outputs. The fluorescence imaging system may optionally be configured with a communication unit 1066, such as a wired or wireless network connection or video output connection for transmitting the time series of fluorescence images as they are being acquired or played back after recording. The communication unit 1066 may additionally or alternatively transmit processed data, such as a spatial map, a subject spatial map, and/or tissue numerical value.

In operation of the exemplary system described in FIGS. 10-12, the subject is positioned relative to fluorescence imaging system 1010 such that an area of interest (e.g., target tissue region) is located beneath the light source 1012 and the image acquisition assembly 1016 such that the illumination module 1020 of light source 1012 produces a substantially uniform field of illumination across substantially the entire area of interest. In some variations, prior to the administration of the fluorescence imaging agent 1014 to the subject, or prior to the fluorescence imaging agent reaching the area of interest, an image may be acquired of the area of interest for the purposes of background deduction. To acquire fluorescence images/subject fluorescence images, the operator of the fluorescence imaging system 1010 may initiate the acquisition of the time series/subject time series of fluorescence images by depressing a remote switch or foot-control, or via a keyboard (not shown) connected to the processor assembly 1018. As a result, the light source 1012 is turned on and the processor assembly 1018 begins recording the fluorescence image data/subject fluorescence image data provided by the image acquisition assembly 1016. When operating in the pulsed mode of the embodiment, the image sensor 1044 in the camera module 1040 is synchronized to collect fluorescence emission following the laser pulse produced by the diode laser 822 in the illumination module 1020. In this way, maximum fluorescence emission intensity is recorded, and signal-to-noise ratio is optimized. In this embodiment, the fluorescence imaging agent 1014 is administered to the subject and delivered to the area of interest via arterial flow. Acquisition of the time series/subject time series of fluorescence images is initiated, for example, shortly after administration of the fluorescence imaging agent 1014, and the time series of fluorescence images from substantially the entire area of interest is acquired throughout the ingress of the fluorescence imaging agent 1014. The fluorescence emission from the region of interest is collected by the collection optics of the camera module 1040. Residual ambient and reflected excitation light is attenuated by subsequent optical elements (e.g., optical element 1050 in FIG. 12 which may be a filter) in the camera module 1040 so that the fluorescence emission can be acquired by the image sensor assembly 1044 with minimal interference by light from other sources.

In some variations, following the acquisition or generation of the time series/subject time series of fluorescence images, the processor assembly 1018 (e.g., processor module 1062 or other processor) may then be initiated to execute instructions stored on memory 1068 and process the imaging data before transmission to the imaging data processing system (e.g., hub 102 of system 100). The system 1010 may transmit, via connection 1066, the spatial map/subject spatial map and/or any clinical correlations or diagnosis derived therefrom or both for display to the user in a composite display feed as, for example, a grayscale or false color image, and/or stored for subsequent use.

A computer program product or tangible non-transitory computer readable medium having computer-executable (readable) program code embedded thereon may provide instructions for causing one or more processors to, when executing the instructions, perform one or more of the methods described herein. Program code can be written in any appropriate programming language and delivered to the processor in many forms, including, for example, but not limited to information permanently stored on non-writeable storage media (e.g., read-only memory devices such as ROMs, CD-ROM disks, etc.), information alterably stored on writeable storage media (e.g., hard drives or the like), information conveyed to the processor through communication media, such as a local area network, a public network such as the Internet, or any type of media suitable for storing electronic instruction. When carrying computer readable instructions that implement the various embodiments of the methods described herein, such computer readable media represent examples of various embodiments. In various embodiments, the tangible non-transitory computer readable medium comprises all computer-readable media, and the present invention scope is limited to computer readable media wherein the media is both tangible and non-transitory.

A kit may include any part of the systems described herein and the fluorescence imaging agent such as, for example, a fluorescence dye such as ICG or any suitable fluorescence imaging agent. In further aspects, a kit may include a tangible non-transitory computer readable medium having computer-executable (readable) program code embedded thereon that may provide instructions for causing one or more processors, when executing the instructions, to perform one or more of the methods for characterizing tissue and/or predicting clinical data described herein. The kit may include instructions for use of at least some of its components (e.g., for using the fluorescence imaging agent, for installing the computer-executable (readable) program code with instructions embedded thereon, etc.). In yet further aspects, there is provided a fluorescence imaging agent such as, for example, a fluorescence dye for use in in the methods and systems described herein. In further variations, a kit may include any part of or the entire system described herein and a fluorescence agent such as, for example, a fluorescence dye such as ICG, or any other suitable fluorescence agent, or a combination of fluorescence agents.

Example Imaging Agents for Use in Generating Imaging Data

According to some embodiments, in fluorescence medical imaging applications, the imaging agent is a fluorescence imaging agent such as, for example, ICG dye. The fluorescence imaging agent, such as ICG, may be pre-administered to the subject, prior to performing the methods as described herein. ICG, when administered to the subject, binds with blood proteins and circulates with the blood in the tissue. The fluorescence imaging agent (e.g., ICG) may be administered to the subject as a bolus injection (e.g., into a vein or an artery) in a concentration suitable for imaging such that the bolus circulates in the vasculature and traverses the microvasculature. In other embodiments in which multiple fluorescence imaging agents are used, such agents may be administered simultaneously, e.g. in a single bolus, or sequentially in separate boluses. The fluorescence imaging agents may be pre-administered to the subject, prior to performing the methods as described herein. In some embodiments, the fluorescence imaging agent may be administered by a catheter. In certain embodiments, the fluorescence imaging agent may be administered less than an hour in advance of performing the measurement of signal intensity arising from the fluorescence imaging agent. For example, the fluorescence imaging agent may be administered to the subject less than 30 minutes in advance of the measurement. In yet other embodiments, the fluorescence imaging agent may be administered at least 30 seconds in advance of performing the measurement. In still other embodiments, the fluorescence imaging agent may be administered contemporaneously with performing the measurement.

According to some embodiments, the fluorescence imaging agent may be administered in various concentrations to achieve a desired circulating concentration in the blood. For example, in embodiments where the fluorescence imaging agent is ICG, it may be administered at a concentration of about 2.5 mg/mL to achieve a circulating concentration of about 5 µM to about 10 µM in blood. In various embodiments, the upper concentration limit for the administration of the fluorescence imaging agent is the concentration at which the fluorescence imaging agent becomes clinically toxic in circulating blood, and the lower concentration limit is the instrumental limit for acquiring the signal intensity data arising from the fluorescence imaging agent circulating with blood to detect the fluorescence imaging agent. In various other embodiments, the upper concentration limit for the administration of the fluorescence imaging agent is the concentration at which the fluorescence imaging agent becomes self-quenching. For example, the circulating concentration of ICG may range from about 2 µM to about 10 mM. Thus, in one aspect, the method comprises the step of administration of the imaging agent (e.g., a fluorescence imaging agent) to the subject and acquisition of the signal intensity data (e.g., video) prior to processing the signal intensity data according to the various embodiments. In another aspect, the method excludes any step of administering the imaging agent to the subject.

According to some embodiments, a suitable fluorescence imaging agent for use in fluorescence imaging applications to generate fluorescence image data is an imaging agent which can circulate with the blood (e.g., a fluorescence dye which can circulate with, for example, a component of the blood such as lipoproteins or serum plasma in the blood) and transit vasculature of the tissue (i.e., large vessels and microvasculature), and from which a signal intensity arises when the imaging agent is exposed to appropriate light energy (e.g., excitation light energy, or absorption light energy). In various embodiments, the fluorescence imaging agent comprises a fluorescence dye, an analogue thereof, a derivative thereof, or a combination of these. A fluorescence dye includes any non-toxic fluorescence dye. In certain embodiments, the fluorescence dye optimally emits fluorescence in the near-infrared spectrum. In certain embodiments, the fluorescence dye is or comprises a tricarbocyanine dye. In certain embodiments, the fluorescence dye is or comprises ICG, methylene blue, or a combination thereof. In other embodiments, the fluorescence dye is or comprises fluorescein isothiocyanate, rhodamine, phycoerythrin, phycocyanin, allophycocyanin, o-phthaldehyde, fluorescamine, rose Bengal, trypan blue, fluoro-gold, or a combination thereof, excitable using excitation light wavelengths appropriate to each dye. In some embodiments, an analogue or a derivative of the fluorescence dye may be used. For example, a fluorescence dye analog or a derivative includes a fluorescence dye that has been chemically modified, but still retains its ability to fluoresce when exposed to light energy of an appropriate wavelength.

In various embodiments, the fluorescence imaging agent may be provided as a lyophilized powder, solid, or liquid. In certain embodiments, the fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. In various embodiments, any diluent or carrier which will maintain the fluorescence imaging agent in solution may be used. As an example, ICG may be reconstituted with water. In some embodiments, once the fluorescence imaging agent is reconstituted, it may be mixed with additional diluents and carriers. In some embodiments, the fluorescence imaging agent may be conjugated to another molecule, such as a protein, a peptide, an amino acid, a synthetic polymer, or a sugar, for example to enhance solubility, stability, imaging properties, or a combination thereof. Additional buffering agents may optionally be added including Tris, HCl, NaOH, phosphate buffer, and/or HEPES.

A person of skill in the art will appreciate that, although a fluorescence imaging agent was described above in detail, other imaging agents may be used in connection with the systems, methods, and techniques described herein, depending on the optical imaging modality. Such fluorescence agents may be administered into body fluid (e.g., lymph fluid, spinal fluid) or body tissue.

In some variations, the fluorescence imaging agent used in combination with the methods, systems and kits described herein may be used for blood flow imaging, tissue perfusion imaging, lymphatic imaging, or a combination thereof, which may performed prior to, during or after an invasive surgical procedure, a minimally invasive surgical procedure, a non-invasive surgical procedure, or a combination thereof. The methods of imaging tissue of a subject, or operating an electronic rolling shutter imager, per se may exclude any invasive surgical step. The method of blood flow imaging, tissue perfusion imaging, lymphatic imaging, or a combination thereof, per se may exclude any invasive surgical step. Examples of invasive surgical procedure which may involve blood flow and tissue perfusion include a cardiac-related surgical procedure (e.g., CABG on pump or off pump) or a reconstructive surgical procedure. An example of a non-invasive or minimally invasive procedure includes wound (e.g., chronic wound such as for example pressure ulcers) treatment and/or management. In this regard, for example, a change in the wound over time, such as a change in wound dimensions (e.g., diameter, area), or a change in tissue perfusion in the wound and/or around the peri-wound, may be tracked over time with the application of the methods and systems. Examples of lymphatic imaging include identification of one or more lymph nodes, lymph node drainage, lymphatic mapping, or a combination thereof. In some variations such lymphatic imaging may relate to the female reproductive system (e.g., uterus, cervix, vulva).

In variations relating to cardiac applications, the imaging agent(s) (e.g., ICG alone or in combination with another imaging agent) may be injected intravenously through, for example, the central venous line, bypass pump and/or cardioplegia line to flow and/or perfuse the coronary vasculature, microvasculature and/or grafts. ICG may be administered as a dilute ICG/blood/saline solution down the grafted vessel such that the final concentration of ICG in the coronary artery is approximately the same or lower as would result from injection of about 2.5 mg (i.e., 1 ml of 2.5 mg/ml) into the central line or the bypass pump. The ICG may be prepared by dissolving, for example, 25 mg of the solid in 10 ml sterile aqueous solvent, which may be provided with the ICG by the manufacturer. One milliliter of the ICG solution may be mixed with 500 ml of sterile saline (e.g., by injecting 1 ml of ICG into a 500 ml bag of saline). Thirty milliliters of the dilute ICG/saline solution may be added to 10 ml of the subject's blood, which may be obtained in an aseptic manner from the central arterial line or the bypass pump. ICG in blood binds to plasma proteins and facilitates preventing leakage out of the blood vessels. Mixing of ICG with blood may be performed using standard sterile techniques within the sterile surgical field. Ten ml of the ICG/saline/blood mixture may be administered for each graft. Rather than administering ICG by injection through the wall of the graft using a needle, ICG may be administered by means of a syringe attached to the (open) proximal end of the graft. When the graft is harvested surgeons routinely attach an adaptor to the proximal end of the graft so that they can attach a saline filled syringe, seal off the distal end of the graft and inject saline down the graft, pressurizing the graft and thus assessing the integrity of the conduit (with respect to leaks, side branches etc.) prior to performing the first anastomosis. In other variations, the methods, dosages or a combination thereof as described herein in connection with cardiac imaging may be used in any vascular and/or tissue perfusion imaging applications.

Lymphatic mapping is an important part of effective surgical staging for cancers that spread through the lymphatic system (e.g., breast, gastric, gynecological cancers). Excision of multiple nodes from a particular node basin can lead to serious complications, including acute or chronic lymphedema, paresthesia, and/or seroma formation, when in fact, if the sentinel node is negative for metastasis, the surrounding nodes will most likely also be negative. Identification of the tumor draining lymph nodes (LN) has become an important step for staging cancers that spread through the lymphatic system in breast cancer surgery for example. LN mapping involves the use of dyes and/or radiotracers to identify the LNs either for biopsy or resection and subsequent pathological assessment for metastasis. The goal of lymphadenectomy at the time of surgical staging is to identify and remove the LNs that are at high risk for local spread of the cancer. Sentinel lymph node (SLN) mapping has emerged as an effective surgical strategy in the treatment of breast cancer. It is generally based on the concept that metastasis (spread of cancer to the axillary LNs), if present, should be located in the SLN, which is defined in the art as the first LN or group of nodes to which cancer cells are most likely to spread from a primary tumor. If the SLN is negative for metastasis, then the surrounding secondary and tertiary LN should also be negative. The primary benefit of SLN mapping is to reduce the number of subjects who receive traditional partial or complete lymphadenectomy and thus reduce the number of subjects who suffer from the associated morbidities such as lymphedema and lymphocysts.

The current standard of care for SLN mapping involves injection of a tracer that identifies the lymphatic drainage pathway from the primary tumor. The tracers used may be radioisotopes (e.g. Technetium-99 or Tc-99m) for intraoperative localization with a gamma probe. The radioactive tracer technique (known as scintigraphy) is limited to hospitals with access to radioisotopes require involvement of a nuclear physician and does not provide real-time visual guidance. A colored dye, isosulfan blue, has also been used, however this dye cannot be seen through skin and fatty tissue. In addition, blue staining results in tattooing of the breast lasting several months, skin necrosis can occur with subdermal injections, and allergic reactions with rare anaphylaxis have also been reported. Severe anaphylactic reactions have occurred after injection of isosulfan blue (approximately 2% of patients). Manifestations include respiratory distress, shock, angioedema, urticarial and pruritus. Reactions are more likely to occur in subjects with a history of bronchial asthma, or subjects with allergies or drug reactions to triphenylmethane dyes. Isosulfan blue is known to interfere with measurements of oxygen saturation by pulse oximetry and methemoglobin by gas analyzer. The use of isosulfan blue may result in transient or long-term (tattooing) blue coloration.

In contrast, fluorescence imaging in accordance with the various embodiments for use in SLN visualization, mapping, facilitates direct real-time visual identification of a LN and/or the afferent lymphatic channel intraoperatively, facilitates high-resolution optical guidance in real-time through skin and fatty tissue, visualization of blood flow, tissue perfusion or a combination thereof.

In some variations, visualization, classification or both of lymph nodes during fluorescence imaging may be based on imaging of one or more imaging agents, which may be further based on visualization and/or classification with a gamma probe (e.g., Technetium Tc-99m is a clear, colorless aqueous solution and is typically injected into the periareolar area as per standard care), another conventionally used colored imaging agent (isosulfan blue), and/or other assessment such as, for example, histology. The breast of a subject may be injected, for example, twice with about 1% isosulfan blue (for comparison purposes) and twice with an ICG solution having a concentration of about 2.5 mg/ml. The injection of isosulfan blue may precede the injection of ICG or vice versa. For example, using a TB syringe and a 30 G needle, the subject under anesthesia may be injected with 0.4 ml (0.2 ml at each site) of isosulfan blue in the periareolar area of the breast. For the right breast, the subject may be injected at 12 and 9 o'clock positions and for the left breast at 12 and 3 o'clock positions. The total dose of intradermal injection of isosulfan blue into each breast may be about 4.0 mg (0.4 ml of 1% solution: 10 mg/ml). In another exemplary variation, the subject may receive an ICG injection first followed by isosulfan blue (for comparison). One 25 mg vial of ICG may be reconstituted with 10 ml sterile water for injection to yield a 2.5 mg/ml solution immediately prior to ICG administration. Using a TB syringe and a 30 G needle, for example, the subject may be injected with about 0.1 ml of ICG (0.05 ml at each site) in the periareolar area of the breast (for the right breast, the injection may be performed at 12 and 9 o'clock positions and for the left breast at 12 and 3 o'clock positions). The total dose of intradermal injection of ICG into each breast may be about 0.25 mg (0.1 ml of 2.5 mg/ml solution) per breast. ICG may be injected, for example, at a rate of 5 to 10 seconds per injection. When ICG is injected intradermally, the protein binding properties of ICG cause it to be rapidly taken up by the lymph and moved through the conducting vessels to the LN. In some variations, the ICG may be provided in the form of a sterile lyophilized powder containing 25 mg ICG with no more than 5% sodium iodide. The ICG may be packaged with aqueous solvent consisting of sterile water for injection, which is used to reconstitute the ICG. In some variations the ICG dose (mg) in breast cancer sentinel lymphatic mapping may range from about 0.5 mg to about 10 mg depending on the route of administration. In some variations, the ICG does may be about 0.6 mg to about 0.75 mg, about 0.75 mg to about 5 mg, about 5 mg to about 10 mg. The route of administration may be for example subdermal, intradermal (e.g., into the periareolar region), subareolar, skin overlaying the tumor, intradermal in the areola closest to tumor, subdermal into areola, intradermal above the tumor, periareolar over the whole breast, or a combination thereof. The injections may be prior to visualization and/or classification. The NIR fluorescent positive LNs (e.g., using ICG) may be represented as a black and white NIR fluorescence image(s) for example and/or as a full or partial color (white light) image, full or partial desaturated white light image, an enhanced colored image, an overlay (e.g., fluorescence with any other image), a composite image (e.g., fluorescence incorporated into another image) which may have various colors, various levels of desaturation or various ranges of a color to highlight/visualize certain features of interest. Processing of the images may be further performed for further visualization and/or other analysis (e.g., quantification). The lymph nodes and lymphatic vessels may be visualized (e.g., intraoperatively, in real time) using fluorescence imaging systems and methods according to the various embodiments for ICG and SLNs alone or in combination with a gamma probe (Tc-99m) according to American Society of Breast Surgeons (ASBrS) practice guidelines for SLN biopsy in breast cancer patients. Fluorescence imaging for LNs may begin from the site of injection by tracing the lymphatic channels leading to the LNs in the axilla. Once the visual images of LNs are identified, LN mapping and identification of LNs may be done through incised skin, LN mapping may be performed until ICG visualized nodes are identified. The method of LN mapping per se may exclude any surgical step. For comparison, mapping with isosulfan blue may be performed until 'blue' nodes are identified. LNs identified with ICG alone or in combination with another imaging technique (e.g., isosulfan blue, and/or Tc-99m) may be labeled to be excised. Subject may have various stages of breast cancer (e.g., IA, TB, IIA).

In some variations, such as for example, in gynecological cancers (e.g., uterine, endometrial, vulvar and cervical malignancies), ICG may be administered interstitially for the visualization of lymph nodes, lymphatic channels, or a combination thereof. When injected interstitially, the protein binding properties of ICG cause it to be rapidly taken up by the lymph and moved through the conducting vessels to the SLN. ICG may be provided for injection in the form of a sterile lyophilized powder containing 25 mg ICG (e.g., 25 mg/vial) with no more than 5.0% sodium iodide. ICG may be then reconstituted with commercially available water (sterile) for injection prior to use. According to an embodiment, a vial containing 25 mg ICG may be reconstituted in 20 ml of water for injection, resulting in a 1.25 mg/ml solution. A total of 4 ml of this 1.25 mg/ml solution is to be injected into a subject (4×1 ml injections) for a total dose of ICG of 5 mg per subject. The cervix may also be injected four (4) times with a 1 ml solution of 1% isosulfan blue 10 mg/ml (for comparison purposes) for a total dose of 40 mg. The injection may be performed while the subject is under anesthesia in the operating room. In some variations the ICG dose (mg) in gynecological cancer sentinel lymph node detection and/or mapping may range from about 0.1 mg to about 5 mg depending on the route of administration. In some variations, the ICG does may be about 0.1 mg to about 0.75 mg, about 0.75 mg to about 1.5 mg, about 1.5 mg to about 2.5 mg, about 2.5 mg to about 5 mg. The route of administration may be for example cervical injection, vulva peritumoral injection, hysteroscopic endometrial injection, or a combination thereof. In order to minimize the spillage of isosulfan blue or ICG interfering with the mapping procedure when LNs are to be excised, mapping may be performed on a hemi-pelvis, and mapping with both isosulfan blue and ICG may be performed prior to the excision of any LNs. LN mapping for Clinical Stage I endometrial cancer may be performed according to the NCCN Guidelines for Uterine Neoplasms, SLN Algorithm for Surgical Staging of Endometrial Cancer; and SLN mapping for Clinical Stage I cervical cancer may be performed according to the NCCN Guidelines for Cervical Neoplasms, Surgical/SLN Mapping Algorithm for Early-Stage Cervical Cancer. Identification of LNs may thus be based on ICG fluorescence imaging alone or in combination or co-administration with for a colorimetric dye (isosulfan blue) and/or radiotracer.

Visualization of lymph nodes may be qualitative and/or quantitative. Such visualization may comprise, for example, lymph node detection, detection rate, anatomic distribution of lymph nodes. Visualization of lymph nodes according to the various embodiments may be used alone or in combination with other variables (e.g., vital signs, height, weight, demographics, surgical predictive factors, relevant medical history and underlying conditions, histological visualization and/or assessment, Tc-99m visualization and/or assessment, concomitant medications). Follow-up visits may occur on the date of discharge, and subsequent dates (e.g., one month).

Lymph fluid comprises high levels of protein, thus ICG can bind to endogenous proteins when entering the lymphatic system. Fluorescence imaging (e.g., ICG imaging) for lymphatic mapping when used in accordance with the methods and systems described herein offers the following example advantages: high-signal to background ratio (or tumor to background ratio) as NIR does not generate significant autofluorescence, real-time visualization feature for lymphatic mapping, tissue definition (i.e., structural visualization), rapid excretion and elimination after entering the vascular system, and avoidance of non-ionizing radiation. Furthermore, NIR imaging has superior tissue penetration (approximately 5 to 10 millimeters of tissue) to that of visible light (1 to 3 mm of tissue). The use of ICG for example also facilitates visualization through the peritoneum overlying the para-aortic nodes. Although tissue fluorescence can be observed with NIR light for extended periods, it cannot be seen with visible light and consequently does not impact pathologic evaluation or processing of the LN. Also, florescence is easier to detect intra-operatively than blue staining (isosulfan blue) of lymph nodes. In other variations, the methods, dosages or a combination thereof as described herein in connection with lymphatic imaging may be used in any vascular and/or tissue perfusion imaging applications.

Tissue perfusion relates to the microcirculatory flow of blood per unit tissue volume in which oxygen and nutrients are provided to and waste is removed from the capillary bed of the tissue being perfused. Tissue perfusion is a phenomenon related to but also distinct from blood flow in vessels. Quantified blood flow through blood vessels may be expressed in terms that define flow (i.e., volume/time), or that define speed (i.e., distance/time). Tissue blood perfusion defines movement of blood through micro-vasculature, such as arterioles, capillaries, or venules, within a tissue volume. Quantified tissue blood perfusion may be expressed in terms of blood flow through tissue volume, namely, that of blood volume/time/tissue volume (or tissue mass). Perfusion is associated with nutritive blood vessels (e.g., micro-vessels known as capillaries) that comprise the vessels associated with exchange of metabolites between blood and tissue, rather than larger-diameter non-nutritive vessels. In some embodiments, quantification of a target tissue may include calculating or determining a parameter or an amount related to the target tissue, such as a rate, size volume, time, distance/time, and/or volume/time, and/or an amount of change as it relates to any one or more of the preceding parameters or amounts. However, compared to blood movement through the larger diameter blood vessels, blood movement through individual capillaries can be highly erratic, principally due to vasomotion, wherein spontaneous oscillation in blood vessel tone manifests as pulsation in erythrocyte movement. In some embodiments, blood flow and tissue perfusion imaging described herein in connection with the systems and methods may be used to image tumor tissue and differentiate such tissue from other tissue.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated. For the purpose of clarity and a concise description features are described herein as part of the same or separate embodiments, however, it will be appreciated that the scope of the invention may include embodiments having combinations of all or some of the features described.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method of imaging tissue of a subject using an electronic rolling shutter imager, the method comprising:
   sequentially resetting rows of pixels of the rolling shutter imager from a first row to a last row;
   sequentially reading charge accumulated at the rows of pixels from the first row to the last row, wherein the first row is read after resetting the last row;
   illuminating the tissue of the subject with illumination light for an illumination period that lasts longer than a vertical blanking period, wherein the vertical blanking period is the period from the resetting of the last row to the reading of the first row; and
   generating an image frame from the readings of charge accumulated at the rows of pixels, wherein at least one reading of charge accumulated at a row of pixels is removed or replaced to generate the image frame.

2. The method of claim 1, wherein the illumination period begins prior to the resetting of the last row.

3. The method of claim 1, wherein the illumination period ends after the reading of the first row.

4. The method of claim 1, wherein the illumination period begins at least when the vertical blanking period begins.

5. The method of claim 1, wherein the illumination period ends at least when the vertical blanking period ends.

6. The method of claim 1, wherein at least a reading of charge accumulated at the first row of pixels is removed or replaced to generate the image frame.

7. The method of claim 1, wherein at least a reading of charge accumulated at the last row of pixels is removed or replaced to generate the image frame.

8. The method of claim 1, wherein the at least one reading of charge accumulated at a row of pixels is replaced by at least one predetermined value to generate the image frame.

9. The method of claim 1, wherein at least one reading of charge accumulated at a row of pixels is removed by cropping to generate the image frame.

10. The method of claim 1, wherein the tissue of the subject is illuminated with visible light and the method further comprises illuminating the tissue of the subject with fluorescence excitation light at least during a subsequent vertical blanking period and generating a fluorescence image frame based on light emitted from the tissue of the subject in response to the fluorescence excitation light.

11. The method of claim 10, further comprising administering a fluorescence imaging agent to the subject prior to generating the fluorescence image frame.

12. The method of claim 10, comprising illuminating the tissue of the subject with fluorescence excitation light and visible illumination light simultaneously during the illumination period.

13. The method of claim 1, wherein illuminating the tissue of the subject with illumination light comprises pulsing the illumination light.

14. The method of claim 13, comprising controlling a pulse width of the pulsed illumination light based on readings of charge accumulated at the rows of pixels during a previous frame.

15. The method of claim 1, wherein the illumination light is generated by at least one LED.

16. The method of claim 1, wherein the rolling shutter imager is part of an endoscopic imager.

17. The method of claim 1, wherein the rolling shutter imager comprises a mechanical shutter and the mechanical shutter remains at least partially open from before the illumination period begins until after the illumination period ends.

18. The method of claim 17, further comprising reducing an amount of light received at the rolling shutter imager by operating the mechanical shutter.

19. The method of claim 1, further comprising adjusting a gain of the rolling shutter imager based on readings of charge accumulated at the rows of pixels during a previous frame.

* * * * *

UNITED STATES PATENT AND TRADEMARK OFFICE
CERTIFICATE OF CORRECTION

| | |
|---|---|
| PATENT NO. | : 11,638,517 B2 |
| APPLICATION NO. | : 16/745154 |
| DATED | : May 2, 2023 |
| INVENTOR(S) | : William Huei Liang Chang et al. |

It is certified that error appears in the above-identified patent and that said Letters Patent is hereby corrected as shown below:

In the Drawings

Sheet 5 of 12:

At FIG. 5, at element 514. Please delete "Skip readout here".

At FIG. 5, to the right of element 514 at the far right, upper corner of the drawing. Please delete "Readout here when integration time > 8.3ms".

Signed and Sealed this
Thirty-first Day of December, 2024

Derrick Brent
*Acting Director of the United States Patent and Trademark Office*